United States Patent
Limon

(10) Patent No.: US 10,898,071 B2
(45) Date of Patent: Jan. 26, 2021

(54) SYSTEM AND METHOD FOR MEASUREMENT OF REFRACTIVE ERROR OF AN EYE BASED ON SUBJECTIVE DISTANCE METERING

(71) Applicant: 6 OVER 6 VISION LTD., Kfar Saba (IL)

(72) Inventor: Ofer Limon, Kfar Saba (IL)

(73) Assignee: 6 OVER 6 VISION LTD.

( * ) Notice: Subject to any disclaimer, the term of this patent is extended or adjusted under 35 U.S.C. 154(b) by 16 days.

(21) Appl. No.: 16/444,254

(22) Filed: Jun. 18, 2019

(65) Prior Publication Data
US 2019/0307324 A1    Oct. 10, 2019

Related U.S. Application Data

(63) Continuation of application No. 15/364,551, filed on Nov. 30, 2016, now Pat. No. 10,702,143, which is a
(Continued)

(51) Int. Cl.
*A61B 3/032* (2006.01)
*A61B 3/036* (2006.01)
*A61B 3/00* (2006.01)

(52) U.S. Cl.
CPC ......... *A61B 3/032* (2013.01); *A61B 3/0025* (2013.01); *A61B 3/0033* (2013.01);
(Continued)

(58) Field of Classification Search
CPC ..... A61B 3/028; A61B 3/0025; A61B 3/0041; A61B 3/02; A61B 3/032; A61B 3/0033; A61B 3/0058; A61B 3/036

See application file for complete search history.

(56) References Cited

U.S. PATENT DOCUMENTS

| 5,596,379 A | 1/1997 | Kaesch |
| 5,668,743 A | 9/1997 | Kushelvesky |

(Continued)

FOREIGN PATENT DOCUMENTS

| BY | 4409 | 3/2002 |
| DE | 10007705 | 9/2001 |

(Continued)

OTHER PUBLICATIONS

Office Action for Indian Patent Application No. 11778/DELNP/2015, dated Aug. 29, 2019, 6 pages.
(Continued)

*Primary Examiner* — Collin X Beatty
(74) *Attorney, Agent, or Firm* — Dorsey & Whitney LLP

(57) ABSTRACT

The method include: (a) displaying at least one dynamic target image of at least one sign over a display area; (b) receiving subjective feedback from the subject indicating that the subject is positioned at a maximum distance of best acuity (MDBA) from the target image, wherein the MDBA is the maximum distance in which the subject recognizes the sign; (c) measuring one or more parameter associated with distance, during the time the subject has reached the MDBA distance, using at least one sensor; (d) estimating the MDBA by estimating the distance between the eye of the subject and the display area in which the target image is displayed by using the sensor data and (e) calculating the refractive error of the eye according to the estimated MDBA and characteristics of the target image.

29 Claims, 24 Drawing Sheets

Related U.S. Application Data continuation of application No. 14/896,418, filed as application No. PCT/IL2014/050506 on Jun. 5, 2014, now Pat. No. 9,549,669.

(60) Provisional application No. 61/831,685, filed on Jun. 6, 2013.

(52) U.S. Cl.
CPC ............ *A61B 3/0058* (2013.01); *A61B 3/036* (2013.01); *A61B 3/0325* (2013.01)

(56) References Cited

U.S. PATENT DOCUMENTS

| | | | |
|---|---|---|---|
| 5,675,399 | A | 10/1997 | Kohayakawa |
| 5,877,841 | A | 3/1999 | Jeon |
| 6,072,443 | A | 6/2000 | Nasserbakht et al. |
| 7,367,675 | B2 | 5/2008 | Maddalena et al. |
| 7,524,065 | B1 | 4/2009 | Ogilvie |
| 9,155,461 | B2 | 10/2015 | Bartlett et al. |
| 9,504,378 | B2 * | 11/2016 | Lee ..................... G02C 13/005 |
| 2004/0105073 | A1 | 6/2004 | Maddalena et al. |
| 2005/0094101 | A1 | 5/2005 | Jordan |
| 2011/0027766 | A1 | 2/2011 | Yoo et al. |
| 2012/0050685 | A1 | 3/2012 | Bartlett et al. |
| 2012/0068998 | A1 | 3/2012 | Hong |
| 2012/0212598 | A1 | 8/2012 | Mowrey et al. |
| 2012/0212706 | A1 | 8/2012 | Chou et al. |
| 2013/0076884 | A1 | 3/2013 | Choukroun |
| 2013/0128229 | A1 | 5/2013 | Huang |
| 2013/0141697 | A1 | 6/2013 | Berry et al. |
| 2014/0268060 | A1 | 9/2014 | Lee et al. |
| 2015/0009475 | A1 | 1/2015 | Clark |
| 2015/0062535 | A1 | 3/2015 | Hawke et al. |
| 2015/0150444 | A1 | 6/2015 | Bex et al. |
| 2016/0120402 | A1 | 5/2016 | Limon |
| 2016/0302661 | A1 | 10/2016 | Alberts et al. |
| 2017/0079523 | A1 | 3/2017 | Limon |

FOREIGN PATENT DOCUMENTS

| | | |
|---|---|---|
| FR | 2966038 | 4/2012 |
| JP | H5-154105 | 6/1993 |
| JP | H05176894 | 7/1993 |
| JP | H11-244239 | 9/1999 |
| JP | 2000-83900 | 3/2000 |
| JP | 2002534145 | 10/2002 |
| JP | 2004537331 A | 12/2004 |
| JP | 2006-263067 | 10/2006 |
| JP | 2007-105097 | 4/2007 |
| JP | 2007097707 | 4/2007 |
| JP | 2007143665 | 6/2007 |
| JP | 2012-525948 | 10/2012 |
| KR | 20040066797 A | 7/2004 |
| KR | 20120049850 A | 5/2012 |
| RU | 2210972 | 8/2003 |
| RU | 2419402 | 5/2011 |
| WO | 0040141 | 7/2000 |
| WO | 0198862 | 12/2001 |
| WO | 2004012591 | 2/2004 |
| WO | 2006029048 | 3/2006 |
| WO | 2008047385 | 4/2008 |
| WO | 2008128192 | 10/2008 |
| WO | 2010117386 | 10/2010 |
| WO | 2010132304 | 11/2010 |
| WO | 2011017329 | 2/2011 |
| WO | 2011161087 | 12/2011 |
| WO | 2012022380 | 2/2012 |
| WO | 2013045531 | 4/2013 |
| WO | 2013/078406 | 5/2013 |

OTHER PUBLICATIONS

Notice of Allowance for Japanese Patent Application No. 2018-233175, dated Oct. 8, 2019, 2 pages.

International Preliminary Report on Patentability for PCT/IL2014/050506, dated Dec. 17, 2015, 7 pages.

International Search Report and Written Opinion for PCT/IL2014/050506, dated Oct. 23, 2014, 13 pages.

Letters to the Editor, J Ournal of the Optical Society of America, vol. 47. No. 6, June 1947, pp. 564-565, 2 pages.

Vitor Fernando Pamplona, "Interactive Measurements and Tailored Displays for Optical Aberrations of the Human Eye", Universidade Federal Do Rio Grande Do Sul Instituto De Informática Programa De Pós-Graduação Em Computação (Thesis presented in partial fulfillment of the requirements for the degree of Doctor of Computer Science), Porto Alegre, Jul. 2012, 169 pages.

Notice of Allowance for U.S. Appl. No. 14/896,418, dated Aug. 31, 2016, 17 pages.

European Search Report for European Patent Application No. 14808041.9 dated Mar. 22, 2017, 6 pages.

Office Action for Chinese Patent Application No. 201480044610.X, dated Jun. 23, 2017, 9 pages (Including 5 pages of English translation).

Office Action for Japanese Patent Application No. 2016-517741, dated Mar. 13, 2018, 3 pages (Including 2 pages of English translation).

Decision to Grant for Russian Patent Application No. 2015152290/14, dated Apr. 6, 2018, 40 Pages (Including 15 pages of English translation).

Office Action for U.S. Appl. No. 15/364,551, dated Jul. 13, 2018, 47 pages.

Office Action for Chinese Patent Application No. 201480044610.X, dated May 15, 2018, 3 pages.

Office Action for Australian Patent Application No. 2014276340, dated Oct. 27, 2018, 4 pages.

Office Action for U.S. Appl. No. 15/364,551, dated Feb. 5, 2019, 34 pages.

Office Action for Australian Patent Application No. 2014276340, dated May 15, 2019, 5 pages.

Office Action for Russian Patent Application No. 2018120718 dated May 17, 2019, 17 pages (Including 8 pages of English translation).

Office Action for Australian Patent Application No. 2014276340, dated Jul. 25, 2019, 4 pages.

Notice of Allowance for U.S. Appl. No. 15/364,551, dated Apr. 22, 2019, 8 Pages.

Notice of Allowance for U.S. Appl. No. 15/364,551, dated Aug. 15, 2019, 9 Pages.

* cited by examiner

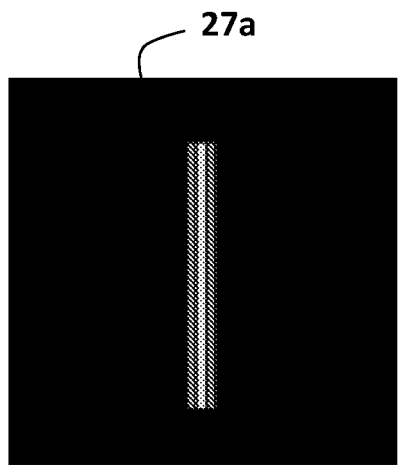
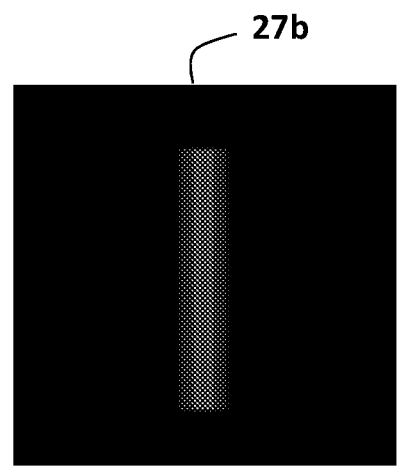
Fig. 8A
Fig. 8B
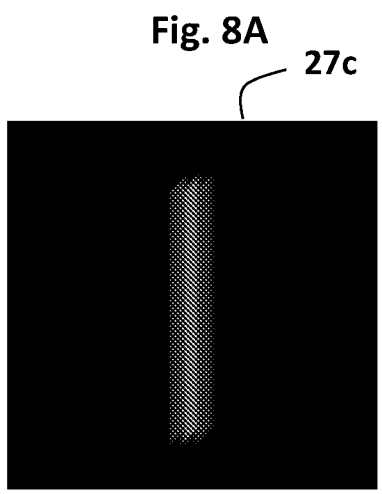
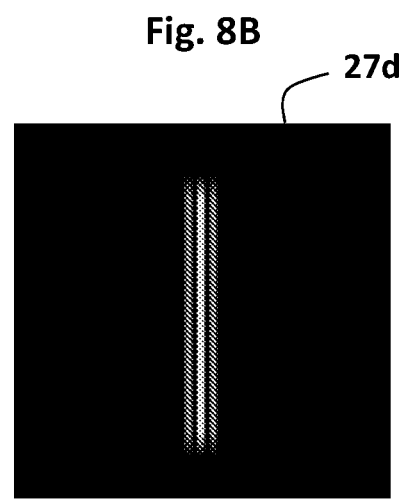
Fig. 8C
Fig. 8D

| Subject refractive error [diopters] | Diopteric error looking at screen at 2m | Size of letter [arcmin] | Name of letter |
|---|---|---|---|
| -1 | -0.5 | 10 | 6/12 |
| -2 | -1.5 | 20 | 6/24 |
| -3 | -2.5 | 32 | 6/36 |
| -4 | -3.5 | 45 | 6/54 |
| -5 | -4.5 | 60 | 6/72 |
| -6 | -5.5 | 70 | 6/84 |

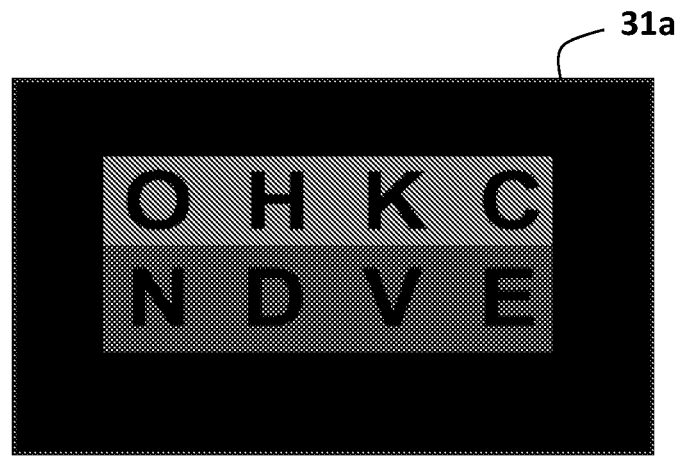
Fig. 14A
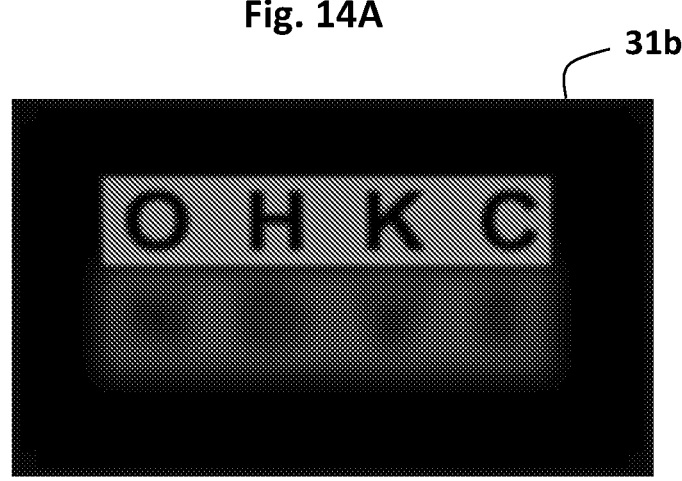
Fig. 14B
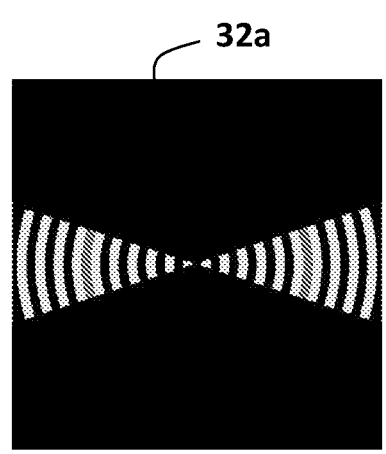 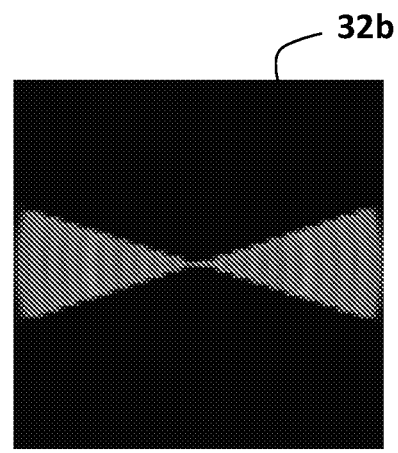
Fig. 15A             Fig. 15B

SYSTEM AND METHOD FOR MEASUREMENT OF REFRACTIVE ERROR OF AN EYE BASED ON SUBJECTIVE DISTANCE METERING

CROSS-REFERENCE TO RELATED PATENT APPLICATIONS

This application is a continuation of U.S. application Ser. No. 15/364,551 filed on Nov. 30, 2016, now issued U.S. Pat. No. 10,702,143, which is a continuation of U.S. application Ser. No. 14/896,418 filed on Dec. 7, 2015, now issued U.S. Pat. No. 9,549,669, which is a national phase entry of International application No. PCT/IL2014/050506, filed Jun. 5, 2014, which claims priority from U.S. provisional patent application No. 61/831,685, filed on Jun. 6, 2013, which are incorporated herein by reference in their entireties.

FIELD OF THE INVENTION

The present invention generally relates to systems and methods for conducting refraction procedure in the optometric examination and particularly to systems and methods for conducting examinations for measuring refractive error.

BACKGROUND OF THE INVENTION

The refraction procedures in the optometric examinations are used to identify various conditions such as refractive error of the eye. The refractive error of an eye (ametropia) is a defect in the ability of the eye to focus parallel rays of light from distant objects on the retina. A distant object is typically viewed at six meters or more from the tested eye. The object used is typically a character such as a letter, number etc. of a predefined size presented over a board or a screen. Refractive error types include myopia, hyperopia and astigmatism.

The refractive error of the eye may be evaluated using subjective or objective methods. Objective methods require a professional examiner to conduct the examination of the patient's eye, using special equipment designed to determine the patient's refractive status and prescribe the appropriate lens (glasses lens and/or contact lens) for each eye.

The subjective method requires the patient to answer specific questions regarding the clarity of a letters/targets presented on a chart at a distance of 6 meters. The examiner interposes lenses of various dioptric powers at a distance of approximately 12 mm from the patient's eye and the patient is required to discern changes in the clarity of the characters by answering forced choice questions. Typically, the patient is asked which of two lens presentations provides the better acuity.

The subjective refraction seeks to find the spherical power and the cylindrical power and axis. Most optometrists and ophthalmologists will use a cross cylinder in conjunction with a trial frame or phoropter in order to determine the cylindrical power and axis. The subjective refraction requires the examiner to interpret the patient's responses.

The objective refraction on the other hand does not require any patient responses. The patient has a passive role while his/her refractive error is evaluated by various possible objective methods and means. Auto refraction and retinoscopy are the most common objective methods. Methods such as photo refraction and aberrometry are also available and used. The less accurate objective refraction usually precedes the subjective result that is used to define the final prescription. An example of a optometric prescription in the minus cyl convention is −2.00/−1.00×90 (sphere −2.00, cyl −1.00, axis 90 deg). In other words, far cyl −2.00 at 180 deg and near cyl −3.00 at 90 deg.

SUMMARY OF THE INVENTION

The present invention provides a method for measuring refractive error of an eye of a subject requiring no refractive correction means. The method comprising, the steps of:

a. displaying at least one selected dynamic or fixed target image over a display area, for each displayed target image, receiving subjective feedback from the subject indicating that the subject is positioned at a maximum distance of best acuity (MDBA) from the target image out of multiple distances experienced by the subject when viewing the target image with one eye thereof, said MDBA being the maximum distance in which the subject clearly recognizes at least one sign or visual effect of said target image, acquiring data associated with distance between the tested eye of the subject and the target image, at least when the subject has reached the MDBA, using at least one sensor, estimating the MDBA according to said acquired data and calculating at least one parameter associated with the refractive error of the tested eye according to the estimated MDBA and according to characteristics of the displayed at least one target image, using at least one processor.

According to some embodiments of the present invention the acquiring data comprises capturing at least one image of the subject's face including the tested eye and a reference shape of known dimensions, using a camera outputting at least one image data, wherein said estimating of the MDBA is carried out by analyzing said image data using a designated software application.

According to some embodiments of the present invention the reference shape is a temporary reference shape taken from an element placed over the non-tested eye.

According to some embodiments of the present invention the reference shape is a constant reference shape, wherein said method further comprises a preliminary process for calibrating absolute dimensions of said constant reference shape using an element with a temporary reference shape of known dimensions.

According to some embodiments of the present invention the different target images are used for testing one or more types of refractive error of the following list: myopia, hyperopia, presbyopia and astigmatism including cylindrical power and cylindrical axis.

According to some embodiments of the present invention a designated optometric testing software application is used, the software operable through said at least one processor of a personal device having a user interface configured for displaying of target images inputting subjective feedback and other input data, instructing the subject and outputting test results.

According to some embodiments of the present invention each of at least one target image is from a list of: at least one single-directional target, at least one multi-directional target, at least one omnidirectional target.

According to some embodiments of the present invention for multidirectional and omnidirectional target images the subject is provided with user interface tools allowing the subject to mark at least one axis indicative of visual acuity of at least one visual effect of the displayed target image for providing the subjective feedback thereof, said marking is used for calculating cylindrical axis of the tested eye, said visual effect identification at a specific distance defines the MDBA of the subject.

According to some embodiments of the present invention the for a single-directional target image the subject is required to indicate as the MDBA the maximal distance at which at least one of the signs of the target image is clearly viewed.

According to some embodiments of the present invention the method further comprises the step of storing and/or outputting the calculated at least one parameter associated with the refractive error of the tested eye.

According to some embodiments of the present invention the at least one target image comprises at least one of the following list:

a target image consisting of a single row of signs of a single color presented over a predefined background of a different color, wherein the MDBA when using this target image is defined as the maximal distance at which the signs are recognizable by the subject;

a target image consisting of a two rows of signs each row having signs each row is presented over a different background color, wherein the MDBA when using this target image is defined as the maximal distance at which the signs of one of the rows are blur and the sings of the other row are distinguishable by the subject;

a papillon target image constructed of curved stripes over a background, where at least some of the stripes are of a first color and at least one of the stripes is of a second color and the background is of a third color, wherein the MDBA when using this target image is defined as the maximal distance at which the at least one stripe of second color retrieves its original color by focusing;

a dual color concentric rings target image or a partial of the concentric rings, wherein the MDBA when using this target image is defined as the maximal distance at which at least a papillon image from the concentric ring shape is clearly visible;

a colored concentric rings target image having rings of at least one color and background of a different color, wherein the MDBA when using this target image is defined as the maximal distance at which at least a papillon image from the concentric ring shape is clearly visible with at least one stripe of second color has not changed its color;

a chromatic sun-shaped target image constructed of multiple stripes elements each element comprises at least one outer stripe of one color and a middle stripe of another color, said elements are radially arranged such as to form a radially symmetrical sun-like shape, wherein the MDBA when using this target image is defined as the maximal distance at which at least some of the elements are clearly visible without change in the second color;

a target image with combined chromatic sun-shaped image and a concentric rings image, said concentric rings image is positioned at a center of the chromatic rings image such as to share the same radial symmetry axis, wherein the MDBA when using this target image is defined as the maximal distance at which at least some of the elements of the chromatic sun image are clearly visible and at least a papillon image of the concentric rings shape is visible without change in the second color of the chromatic sun image; and/or a unique pattern target image where the basic block is elliptical tilted shape, replicated row-wise and column-wise while interchanging its color in every dimension, wherein at least one dark line obstructing completely or partially at least one part of the row of the pattern or at least one perturbation region to the basic periodic structure.

According to some embodiments of the present invention the refractive error is measured through a process comprising: Measuring roughly estimated (RE) sphere equivalent power.

According to some embodiments of the present invention the method further comprising a correction process for correcting cylindrical and spherical power, said correction process comprising the steps of: receiving astigmatism angle, cylindrical power and spherical power resulting from previous testing of the subject, displaying the unique pattern target image over the display area rotated to an angle of astigmatism of the subject, according to the received astigmatism angle, said unique pattern target image is displayed over the display area at at least two sizes, each size calculated according to the received cylindrical power and spherical power, for each size of the displayed unique pattern target image, instructing the subject to distance from the target image until recognizing a predefined visual effect in which the presence of at least one alternating green-red patterns or red-yellow pattern are best apparent:

for each size of the displayed unique pattern target image, measuring the distance between the unique pattern target image and the tested eye of the subject; and recalculating cylindrical power and spherical power according to the measured distances.

The present invention provides a system for measuring refractive error of an eye of a subject requiring no refractive correction means. The system comprising: at least one display unit defining a display area for displaying target images thereover, at least one sensor for sensing at least one measurable parameter in a repeatable manner, said parameter allows directly or indirectly measuring distance between the subject and the display area and at least one processor having a designated application operable thereby configured for:

receiving data from said sensor in real time;

receiving subjective feedback from the subject, through a user interface of said application, said feedback includes indication that the subject is positioned at a maximum distance of best acuity (MDBA) from the target image out of multiple distances experienced by the subject, when viewing the target image with one eye thereof, said MDBA being the maximum distance in which the subject clearly recognizes at least one sign or visual effect of said target image;

estimating the MDBA by estimating the distance between the eye of the subject and the display area in which the target image is displayed by using data outputted from the sensor; and calculating at least one parameter associated with the refractive error of the tested eye according to the estimated MDBA and characteristics of the displayed target image.

According to some embodiments of the present invention the designated application is operable through a personal device comprising the processor and display unit, wherein said at least one sensor is communicable and controllable by said personal device.

According to some embodiments of the present invention the designated application is operable through a personal device comprising the processor, the at least one sensor and the display unit.

According to some embodiments of the present invention the at least one sensor comprises a stills or video camera controllable by said software application and configured for capturing at least one image of the subject's face including the tested eye and a reference shape of known dimensions, wherein said estimating of the MDBA is carried out by analyzing said image data using a designated software application.

According to some embodiments of the present invention the reference shape is a temporary reference shape taken from an element placed over the non-tested eye.

According to some embodiments of the present invention the said reference shape is a constant reference shape, wherein said method further comprises a preliminary process for calibrating absolute dimensions of said constant reference shape using an element with a temporary reference shape of known dimensions.

According to some embodiments of the present invention the different target images are used for testing one or more types of refractive error of the following list: myopia, hyperopia, presbyopia and astigmatism, including cylindrical power and cylindrical axis.

According to some embodiments of the present invention the each of said at least one target image is from a list of: at least one single-directional target, at least one multi-directional target; at least one omnidirectional target.

According to some embodiments of the present invention the multidirectional and omnidirectional target images the subject is provided with user interface tools allowing the subject to mark at least one axis indicative of visual acuity of at least one visual effect of the displayed target image for providing the subjective feedback thereof, said marking is used for calculating cylindrical axis of the tested eye, said visual effect identification at a specific distance defines the MDBA of the subject.

According to some embodiments of the present invention, a single-directional target image the subject is required to indicate as the MDBA the maximal distance at which at least one of the signs of the target image is clearly viewed.

According to some embodiments of the present invention the system further comprising a storage unit for storing the calculated at least one parameter associated with the refractive error of the tested eye.

The present invention provides a method for measuring refractive error of an eye of a subject requiring no refractive correction means. The method comprising: conducting a preliminary test for roughly estimating visual acuity of each tested eye of the subject, conducting a far cylindrical error test using at least one target image having multidirectional or omnidirectional symmetry for detecting cylindrical axis, and conducting a far and near cylindrical error test using at least one target image having single directional or multidirectional or omnidirectional symmetry for detecting cylindrical power, wherein each of said tests are conducted by:

displaying at least one selected dynamic or fixed target image over a display area;

for each displayed target image, receiving subjective feedback from the subject indicating that the subject is positioned at a maximum distance of best acuity (MDBA) from the target image out of multiple distances experienced by the subject when viewing the target image with one eye thereof, said MDBA being the maximum distance in which the subject clearly recognizes at least one sign or visual effect of said target image;

acquiring data associated with distance between the tested eye of the subject and the target image, at least when the subject has reached the MDBA, using at least one sensor;

estimating the MDBA according to said acquired data; and calculating at least one parameter associated with the refractive error of the tested eye according to the estimated MDBA and according to characteristics of the displayed at least one target image, using at least one processor.

According to some embodiments of the present invention the preliminary test is configured for roughly measuring sphere equivalent power (SEP) of the tested eye.

According to some embodiments of the present invention the far cylindrical error test is conducted by using a chromatic sun shaped target image constructed of multiple stripes elements each element comprises at least one outer stripe of one color and a middle stripe of another color, said elements are radially arranged such as to form a radially symmetrical sun-like shape, wherein the MDBA when using this target image is defined as the maximal distance at which at least some of the elements are clearly visible without a perceivable change in original color;

wherein for multidirectional and omnidirectional target images the subject is provided with user interface tools allowing the subject to mark at least one axis indicative of visual acuity of at least one visual effect of the displayed target image for providing the subjective feedback thereof, said marking is used for calculating cylindrical axis of the tested eye, said visual effect identification at a specific distance defines the MDBA of the subject According to some embodiments of the present invention the near cylindrical error test is conducted by using a papillon shaped target image constructed of curved stripes over a background, where at least some of the stripes are of a first color and at least one of the stripes is of a second color and the background is of a third color, wherein the MDBA when using this target image is defined as the maximal distance at which the at least one stripe of second color sharpens without changing its color.

According to some embodiments of the present invention the method further comprising at least one of: at least one refinement test for refining measurements of said far cylindrical error, at least one refinement test for refining measurements of said near cylindrical error and at least one refinement test for refining measurements of said near cylindrical axis.

According to some embodiments of the present invention the refinement test for measuring far cylindrical error is carried out by using at least one of the following target images:

a target image consisting of a single raw of signs of a single color presented over a predefined background of a different color, wherein the MDBA when using this target image is defined as the maximal distance at which the signs are recognizable by the subject;

a target image consisting of a two rows of signs each row having signs each row is presented over a different background color, wherein the MDBA when using this target image is defined as the maximal distance at which the signs of one of the rows are blur and the sings of the other row are distinguishable by the subject;

a papillon target image constructed of curved stripes over a background, where at least some of the stripes are of a first color and at least one of the stripes is of a second color and the background is of a third color, wherein the MDBA when using this target image is defined as the maximal distance at which the at least one stripe of second color retrieves its original color by focusing;

a dual color concentric rings target image or partial area of the concentric rings, wherein the MDBA when using this target image is defined as the maximal distance at which at least a papillon image from the concentric ring shape is clearly visible;

a colored concentric rings target image having rings of at least one color and background of a different color, wherein the MDBA when using this target image is defined as the maximal distance at which at least a papillon image from the concentric ring shape is clearly visible with at least one stripe of second color has not changed its color;

a chromatic sun-shaped target image constructed of multiple stripes elements each element comprises at least one outer stripe of one color and a middle stripe of another color, said elements are radially arranged such as to form a radially symmetrical sun-like shape, wherein the MDBA when using this target image is defined as the maximal distance at which at least some of the elements are clearly visible without change in the second color;

a target image with combined chromatic sun-shaped image and a concentric rings image, said concentric rings image is positioned at a center of the chromatic rings image such as to share the same radial symmetry axis, wherein the MDBA when using this target image is defined as the maximal distance at which at least some of the elements of the chromatic sun image are clearly visible and at least a papillon image of the concentric rings shape is visible without change in the second color of the chromatic sun image; and/or a unique pattern target image where the basic block is elliptical tilted shape, replicated row-wise and column-wise while interchanging its color in every dimension, wherein at least one dark line obstructing completely or partially at least one part of the row of the pattern or at least one perturbation region to the basic periodic structure.

According to some embodiments of the present invention the method further comprising a correction process for correcting cylindrical and spherical power, said correction process comprising the steps of:

receiving astigmatism angle, cylindrical power and spherical power resulting from previous testing of the subject;

displaying the unique pattern target image over the display area rotated to an angle of astigmatism of the subject, according to the received astigmatism angle, said unique pattern target image is displayed over the display area at at least two sizes, each size calculated according to the received cylindrical power and spherical power;

for each size of the displayed unique pattern target image, instructing the subject to distance from the target image until recognizing a predefined visual effect;

for each size of the displayed unique pattern target image, measuring the distance between the unique pattern target image and the tested eye of the subject; and recalculating cylindrical power and spherical power according to the measured distances.

According to some embodiments of the present invention the sensor is at least one of proximity sensor, accelerator sensor, camera or 3-dimensional (3D) sensor.

BRIEF DESCRIPTION OF THE DRAWINGS

FIG. 3A shows how the subject carries out a preliminary calibration process using a credit card as a reference shape element; and FIG. 3B shows how the target image is presented over a display area of the smartphone touch screen for allowing the subject to adjust the distance between his/her eye and the target image until reaching maximal distance of best acuity (MDBA).

FIG. 4A shows a target image containing letters with diagonal stripes pattern at a certain angle over a gray background; FIG. 4B shows a target image containing letters with diagonal stripes pattern at a certain angle over a green background; FIG. 4C shows a target image containing letters with diagonal stripes pattern at a certain angle over a red background; FIG. 4D shows a target image containing letters with blurred diagonal stripes pattern at a certain angle in which the stripes blurred shade is blended with the red background; FIG. 4E shows a target image containing letters with diagonal stripes pattern at a certain angle over a blue background; FIG. 4F shows a target image containing white clear letters over a black background; FIG. 4G shows a target image of concentric white circles over a black background; FIG. 4H shows a target image containing a pattern of crossing perpendicular white lines over a black background; FIG. 4I shows a target image containing a pattern of crossing perpendicular lines over a black background, where the horizontal lines are green and the vertical lines are red; FIGS. 4J-4L show a black and white (BW) target image with concentric rings: FIG. 4J shows the image as displayed over the screen, where FIGS. 4K and 4L show how the image will be perceived by a subject having an astigmatism.

FIGS. 8A-8D show a target for measuring axis of astigmatism using a chromatic method: FIG. 8A shows a colored stripes target for astigmatism measurements that includes three vertical parallel lines the middle one is green and the two outer lines are red, over a black background, where the lines are separated from one another at a known separation difference; FIG. 8B shows how the target of FIG. 8a will be perceived by a subject having angle of astigmatism of 0° (using the minus cyl convention); FIG. 8C shows how the target of FIG. 8A will be perceived by a subject having angle of astigmatism of 45°; and FIG. 8D shows how the target of FIG. 8A will be perceived by a subject having astigmatism that is co-aligned with the direction of the presented colored stripes;

FIG. 9A shows a colored stripes target for astigmatism measurements that includes four sets of stripes each set includes three parallel red-green-red stripes separated equally distance separated, where the sets of stripes angularly cross one another, over a black background; FIG. 9B shows how the target of FIG. 9A will be perceived by a subject having angle of astigmatism of $\alpha_1$; and FIG. 9C shows how a change made to the target of FIG. 9A will be perceived by a subject to indicate the angle of the astigmatism in higher angular precision.

FIG. 13A shows a BW target image of optotypes for measuring myopia through measuring of sphere equivalent power (SEP) of subjects' eyes; and FIG. 13B shows a table for showing how the MDBA is roughly correlated to the letter size and.

FIGS. 14A and 14B show a target image of two sets of black letters one over a blue background and the other over a red background for measuring SEP of subjects eyes, according to some embodiments of the invention: FIG. 14A shows the target image as displayed over the screen for testing SEP; and FIG. 14B shows how the target image of FIG. 14A will be perceived at MDBA distance when only the optotypes letters in blue are blurred and the red ones are readable.

FIGS. 15A and 15B show a striped papillon target image having green arch-shaped stripes over black background with one of the arch-shaped stripes in each side colored in red, according to some embodiments of the invention: FIG. 15A shows the papillon target image as displayed over the screen for measuring the MDBA for the near cyl; and FIG. 15B shows the papillon target image as it would appear prior to passing the MDBA for the near cyl, where the red color appears yellowish. Upon reaching the near cyl MDBA the yellow arch shaped stripe will turn red.

FIG. 16A shows the target image as displayed over the screen for measuring astigmatism; and FIG. 16B shows the target image as it would appear for a subject having a 180 degrees astigmatism.

FIG. 17A shows the target image as displayed over the screen for measuring astigmatism; and FIG. 17B shows the target image as it would appear for a subject having a 180 degrees astigmatism.

FIG. 18A shows the sun target image as displayed over the screen for measuring astigmatism; and FIG. 18B shows the sun target image as it would appear for a subject having a 180 degrees astigmatism.

FIG. 19A shows the combined sun target image as displayed over the screen for measuring astigmatism; and FIG. 19B shows the combined sun target image as it would appear for a subject having a 180 degrees astigmatism.

FIG. 20A shows the concentric rings target image as displayed over the screen for measuring astigmatism; and FIG. 20B shows the concentric rings target image as it would appear for a subject having a 180 degrees astigmatism with a bat marker placed by the subject over the image in a location indicating the center of the papillon shape appearing clearer as input feedback according to which the astigmatism angle of the subject can be deduced.

FIG. 21A shows a target image having interchanging sets of rows of yellow and red elliptic units arranged in rows that are tilted in interchanging directions, where the target image is sliced by two upper and lower thick black stripes and a middle black stripe of a thinner thickness than the upper and, lower stripes; and FIG. 21B shows a unique pattern target image where the basic block is elliptical tilted shape, replicated row-wise and column-wise while interchanging its color in every dimension, wherein at least one dark line obstructing completely or partially at least one part of the row of the pattern or at least one perturbation region to the basic periodic structure. The obstruction or perturbation results in an identical adjacent color of basic block in either a horizontal or vertical direction. Alternatively, the color of basic block lying in perturbed row or beyond obstructed row is similar to its closest neighbor in unperturbed/unobstructed row. When undergoing a certain blur the image have several distinct features as shown in 701a FIG. 22 shows a zoomed image of the pattern of the target images of FIGS. 21A and 21B tilted in one of the possible interchanging directions.

FIG. 24B illustrates how the building blocks of the pattern will blur (arrow shows direction of blur) at distance from the target image for a subject having no astigmatism; and FIG. 24A illustrates how the building blocks of the pattern will blur at distance from the target image for a subject having astigmatism.

FIG. 27B is a continuation of the process of FIG. 27A.

DETAILED DESCRIPTION OF SOME EMBODIMENTS OF THE INVENTION

Figure 1:
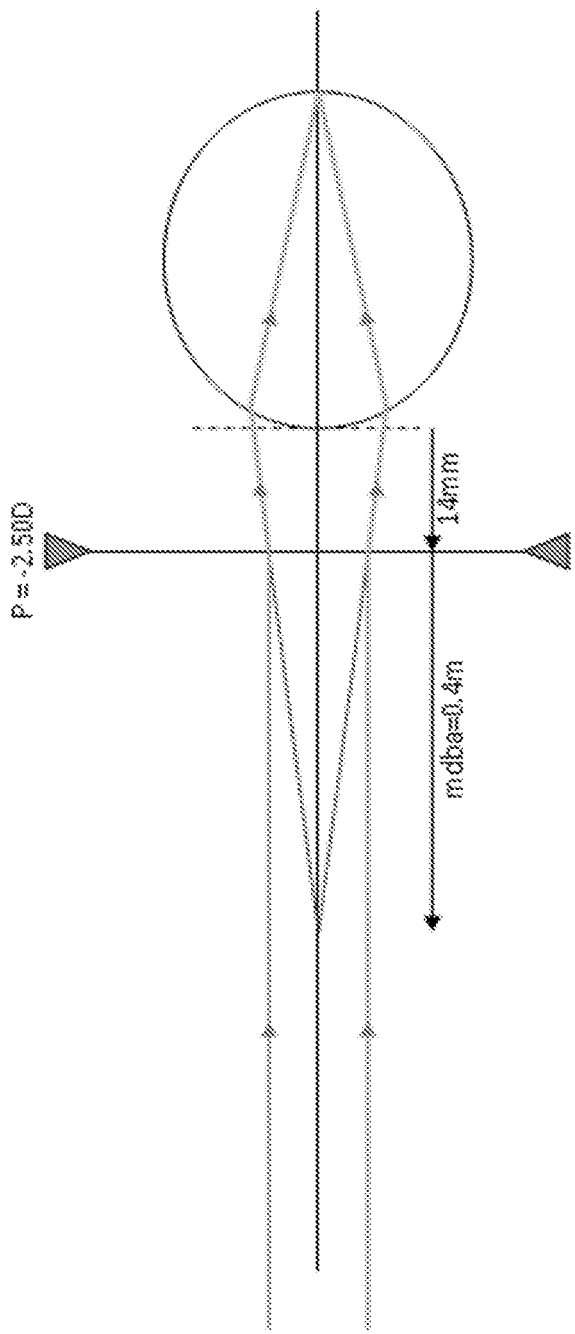
FIG. 1 shows a diagram illustrating maximum distance of best acuity (MDBA) of 0.414 m for a myopic patient having a spectacle refractive error correction power of −2.50 Diopters [D].

In the following detailed description of various embodiments, reference is made to the accompanying drawings that form a part thereof, and in which are shown by way of illustration specific embodiments in which the invention may be practiced. It is understood that other embodiments may be utilized and structural changes may be made without departing from the scope of the present invention.

The present invention, in some embodiments thereof, provides systems and methods for allowing users to carry out accurate eye examinations for measuring refractive error of their eyes or other people's eyes, requiring no refraction correction means such as glasses lenses or contact lenses.

The term "refractive error" also known as "refraction error" as known in the art refers to any type of error in focusing parallel rays of light over the retina of the eye this condition is known as "ametropia". Ametropia includes any one or more of myopia, hyperopia and/or astigmatism, typically categorized as spherical errors and cylindrical errors. Spherical errors include myopia, hyperopia and presbyopia while cylindrical errors include astigmatism. Typical eye test for providence of corrective lenses measure sphere power, astigmatism power and axis related to a certain eye.

According to some embodiments the system allows the subject to self-examine himself for refractive error by using an integrated personal device, or other remote processing unit, or system such as a personal computers (PC), laptop, smartphone, tablet device and the like, provided that the personal device is equipped or communicative with devices that allow display of images, storage, processing, input and output of data and optionally also one or more sensors that allow deducting the distance between the tested eye and the displayed images.

The system includes a display device capable of visually displaying target images over a display area and one or more sensors for enabling measuring at least one parameter that can be used to deduce distances. In other embodiments, distance can be measured directly through the sensor(s) while in other embodiments the distance is measured by using a camera connected to or embedded in the personal device for deducing the distance between the image display and the tested eye of the subject.

The system and method of the present invention, according to some embodiments thereof allow a subject who wishes to make a self refractive error test using a personal device having visual display means such as a screen and a sensor such as video and/or stills camera, wherein the device operates a designated ocular refraction testing software application configured for displaying at least one selected dynamic or fixed target image over the display area; receiving subjective feedback from the subject indicating that the subject is positioned at a maximum distance of best acuity (MDBA) from the target image out of multiple distances experienced by the subject, wherein said MDBA is the maximum distance at which the subject clearly recognizes the displayed target image with one eye of the subject that is tested; measuring at least one parameter associated with distance, when the subject has reached the MDBA, using the sensor; estimating the MDBA by estimating the distance between the tested eye of the subject and the display area in which the target image is displayed by using data outputted from the sensor and a processor of the personal device for carrying out this estimation; and calculating the refractive error of the eye according to the estimated MDBA and characteristics of the target image.

Once the subject indicates through the feedback thereof that he/she has reached the MDBA, the system automatically estimates the actual distance between the subject's tested eye and the presented target image (e.g. center of screen) by using data arriving from the sensors and optionally calibration data taken from a preliminary calibration process for calculating the refractive error of the tested eye, using a designated algorithm. The refractive error is calculated according to the estimated MDBA (which is the estimated distance between the eye and the target image at the time the subject indicated reaching his/her MDBA) and the graphical and other characteristics of the one or more signs in the target image (e.g. size, color, pattern and the like) which, for example results in the dioptric power (also referred to herein as "sphere equivalent power (SEP) and/or sphere power and/or far cylindrical (cyl) power and/or near cyl power).

The display device is any device configured for visually displaying images over a display area such as a screen, a projector device (with or without a screen) and the like. The display device and display area can be embedded in the personal device.

The sensor, which may be embedded in the personal device or communicative therewith in any other configuration, includes for example, one or more video and/or stills cameras, 3-dimensional (3D) sensor configured for mapping surfaces in 3D points or any other optical or other type of sensor for measuring one or more parameters that allow deducing distances or any other sensor or device that allows capturing images or measuring directly or indirectly distance between objects. The algorithm in the system for estimating the actual distance between the tested eye of the subject and the displayed target image is adapted to the specific sensor used and specific output characteristics thereof. For instance, for a stills camera or video camera the algorithm is designed to receive input of the image data outputted by the camera and use the reference image or another image in the image data of known dimensions to calculate the distance of the tested eye at the moment the image was captured by the camera.

According to some embodiments, the present invention provides a designated computer application operable through the personal device of the subject that provides a user interface (UI) that allows a subject to measure his/her own eye refractive error therethrough. This means that the application does not require the subject to try on different correcting lenses for measuring his/her glasses number, cylinder measure and the like.

The application may be designed such that it uses the processing means of the personal device of the subject for the entire examination process (including receiving input, processing and outputting test results and storing data) or communicates with a remote server that is configured for receiving input data through the application from the personal device of the subject, process the data to calculate the subject's refractive error of the tested eye and sending the results to the personal device through this application for being outputted (e.g. presented) to the subject through output means of the personal device (such as through the screen and/or through the speakers of the device).

According to some embodiments, the methods and systems allow the subject to initiate a subjective refraction exam using his/her personal device by accessing a designated application operable thereby (e.g. installed therein or accessed therethrough). Once the session is initiated, a dynamic or static preselected target image is presented over the display area. The target image may be of a shape or a predetermined sign such as a letter, a number and the like known to the subject, where characteristics of the image such as size, pattern color, background and the like, may vary depending on the parameter and/or type of the refractive error that is being tested such as astigmatism, myopia or hyperopia.

As mentioned above, one or more sensors such as a camera embedded or connected to the personal device repeatedly or continuously detect one or more parameters associated with distance and the data of the one or more parameters from the sensor are used for estimating the distance between the subject's tested eye and the display area in which the selected image is displayed. The application UI allows receiving subjective feedback from the subject regarding the displayed image for calculating one or more values of one or more quantifiable parameters indicative of one or more aspects of the refractive error of the tested eye of the subject, also referred to in this document as the result(s) of the examination. These results are then presented to the subject or outputted in any other way through output device(s) of the personal device such as presented over the screen via the UI of the designated application.

According to some embodiments of the invention, a calibration process is used, especially yet not exclusively in the cases in which the sensor is a device for capturing 2D images such as a stills and/or video camera. In these embodiments, a reference shape of known absolute dimensions is used, by using for instance an object of known 3D dimensions or an object having a 2D physical pattern attached thereto or printed thereover that can be identified through image analysis of an acquired image including the pattern reference shape. The known dimensions of the reference shape can be used to deduce the distance between the reference shape's physical position and the camera or the center of the display area associated therewith at the time the image of the reference shape was acquired.

This calibration process may be repeated (continuously or discretely) throughout the examination session, requiring the subject to hold the reference shape in the same position in respect to the position of the tested eye during the entire session or when required by the UI when the measurements are executed. In this way the distance between the tested eye and the presented image is constantly measured or estimated through other measured parameters during the examination session for allowing giving the most accurate results.

In other embodiments the calibration process uses an element consisting of a temporary reference shape such as a credit card having a magnetic stripe reference shape of known dimensions, to study absolute dimensions of a constant reference shape such as one or more facial features of the subject such as the width of the eye (not covered by the temporary reference shape) thereof for allowing using the facial feature absolute value for distance metering in the actual refractive error examination session. This will allow the subject to be free from holding the element of the temporary reference shape throughout the procedure.

According to some embodiments, the UI is configured to output feedback questions and instructions to the subject that are predefined and associated with the specific presented target image and its characteristics to help determine the specific refractive error (e.g. dioptric power) in respect to the estimated MDBA and the target image characteristics.

According to embodiments of the invention, once the test sign or any other target image is presented over the display area at the selected size, the application requires the subject to move the display area (embedded in the device) or to move in respect to the display area (e.g. if the display area is difficult to be moved) to the maximum distance in which he/she still clearly recognizes the one or more signs presented in the target image with a relative acuity. This distance will be defined as the "MDBA", which is proportional to the power (in Diopters) of the corrective lens that will be required. The ratio between the MDBA and the power "P" is calculated by using the following transformation formula:

$$P[\text{Diopters}] = K \frac{1}{MDBA[m]}$$

The power "P" is either average of the subject astigmatic powers (best sphere) or one of the astigmatic powers, depending on the used target that is the shape or pattern of the presented image. For instance, a target with no directionality defined features will cause focusing at a distance corresponding to the mean of astigmatic powers, and a target with features in the direction of one of the astigmatic axes will cause focusing at a distance corresponding to this astigmatic power. K is a calibration constant found in clinical trials and is approximately −1.

According to some embodiments, the subject is required to leave the untested eye wide open (although occluded by the reference shape element e.g. the credit card) during the measuring session as it may effect on the refractive error of the tested eye.

FIG. 1 shows a diagram illustrating maximum distance of best acuity (MDBA) of 0.414 m for a short-sighted patient having a spectacle refractive error correction power of −2.50 Diopters [D].

The sensor of the system is located at a fixed known distance from the location of the presented image, as these two devices (e.g. the screen and the camera) are each fixed to a certain position.

When no refractive correction is set, a relaxed eye, corresponding to contact lenses correction of −2.50 for example, will see a blurred image at a distance further than 0.4 m and first high visual acuity image will be seen at a distance equals to 0.4 m. An image at a distance set between the range (of infinity-400 mm for this example) will be blurred as a function of the vergence $$\left(\frac{1}{\text{Object Distance}[m]}\right)$$

where maximum blur will be evident at infinity and the blur will gradually be reduced along the vergence to reach minimum blur at 0.4 m. An image blur at a distance closer than 0.4 m in this example will depend on the eye's ability to accommodate. If an accommodation of +7 diopters is present, the subject would be able to see high visual acuity image at distance in the range of 400 mm to 105 mm.

Figure 2:
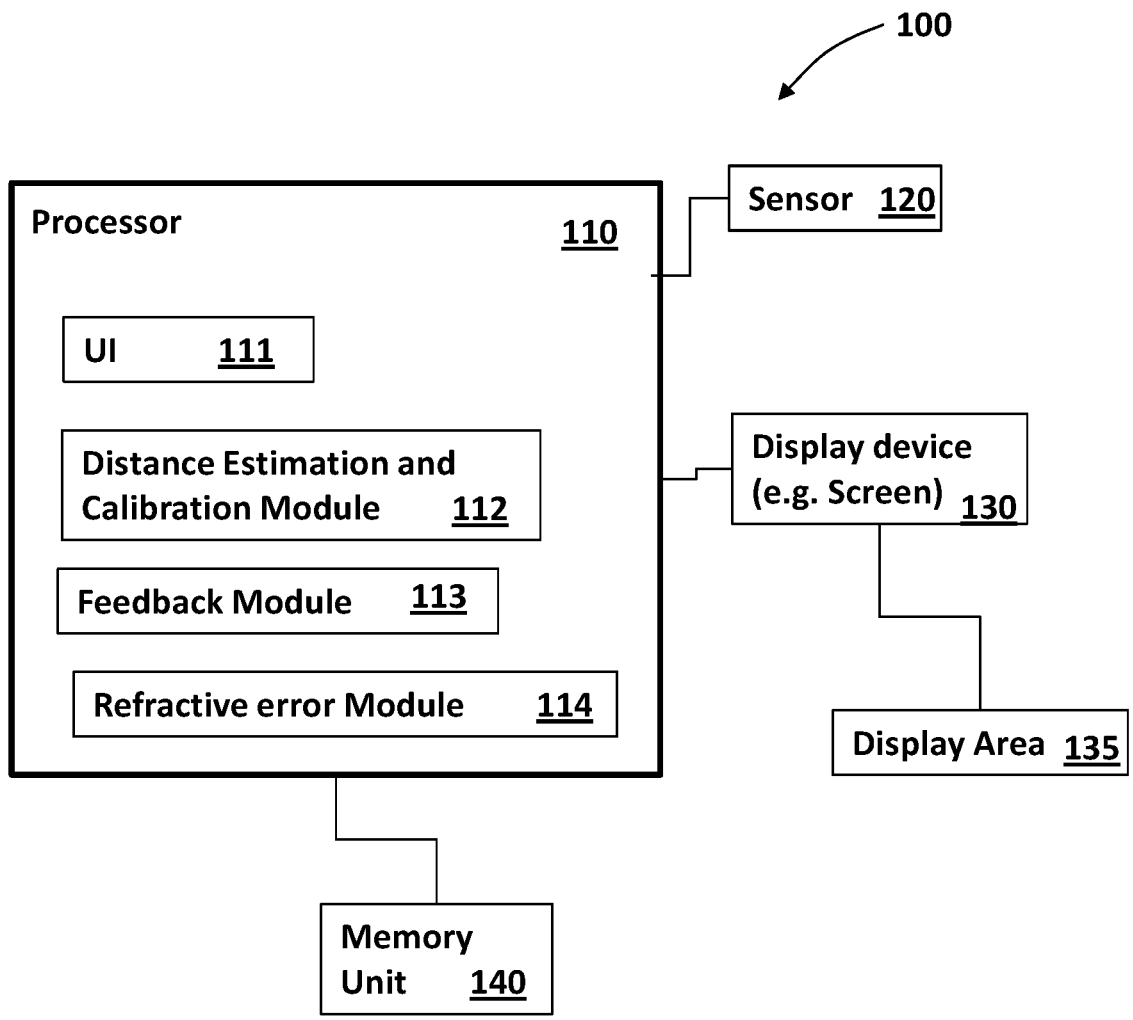
FIG. 2 shows a block diagram of a system for measuring refractive error of a subject's eye, according to some embodiments of the invention.

Reference is now made to FIG. 2 showing a block diagram, schematically illustrating a system 100 for measuring a refractive error of a subject's eye using a computerized system having at least one processor 110 such as a PC computer system, a tablet device or a mobile device having input and output means and a sensor 120 such as a camera that is configured for acquiring 2D frames, and a screen 130 as a display device defining a display area 135 therein.

The processor 110 operates a designated application capable of operating several modules: (i) a user interface (UI) 111; (ii) a distance estimation and calibration module 112 for repeatedly (continuously or discretely) estimating the distance between the tested eye and the display are/presented target image; (iii) feedback module 113 for instructing the subject during an examination session and for allowing the subject to input his/her feedback; and a refractive error module 114 for calculating the refractive error parameter(s) value(s), according to the estimated distance and the characteristics of the presented target images.

According to some embodiments, the UI 111 may be a graphical user interface (GUI) of the designated application, configured for providing a platform for fixedly or dynamically presenting target images, allowing the subject to initiate examination sessions therethrough, instructing the subject during the examination session, allowing the subject to input subjective feedback in response to the presented target image and/or his/her location in respect thereto and for presenting the results of the calculated refractive error.

According to some embodiments, the distance estimation and calibration module 112 is configured for instructing the subject to position himself/herself or the display device/area 130/135 to the MDBA according to his/her subjective perspective and receiving data outputted by the sensor 120 for processing thereof to deduce (estimate) the distance "Di" between the subject's tested eye and the target image at each given moment or timeframe. In cases in which the output of the sensor 120 is an image (e.g. when using a 2D camera), an image analysis process may be initiated to assess the distance by measuring the image-size of a shape in the acquired image that has known dimensions. In these cases the estimation and calibration module 112 (through the UI 111) may instruct the subject to hold a reference shape of known 2D dimensions (such as a credit card having a standard size magnetic stripe with the magnetic stripe facing the camera sensor 120) over his untested eye so that the image acquired by the camera sensor 120 includes the entire 2D known reference shape at each given moment of the examination. In this way the difference between image-size of the reference shape and the known real size thereof allow deducing the distance and angular perspective between at least the camera and the physical element which is or contains the 2D reference shape. This distance and angle allow in turn to estimate the distance between the tested eye located adjacent to the eye covered by the reference shape element and the center of the display area by knowing the positioning of the display area in respect to the camera sensor.

In cases in which a 2D sensor 120 is used, to improve accuracy in distance estimations, a preliminary calibration process may be required, by acquiring an image of the subject holding the reference shape element covering his/her untested eye and measuring the absolute dimensions and shape of the tested eye through an image analysis process, according to the known absolute dimensions of the reference shape. In these embodiments, once the absolute dimensions and shape of the tested eye are calculated the tested eye itself serves as the reference shape in the examination process.

For example, the subject may be required to hold a credit card over one of his/her eyes, with its magnetic stripe of the credit card facing the camera for a preliminary calibration of the examination session and acquire a calibration image capturing both his/her eye (one covered by the credit card) using the camera. The absolute width and length of the magnetic stripe of a credit card is typically standard and will be known in the system. The acquired calibration image is then analyzed, for instance, by calculating a ratio scale (for length width and/or width) according to which the absolute width of the tested eye may be deduced. This Eye-Width (EW) value (e.g. in centimeters) may be stored in a storage unit of the system and used as the known size of the tested eye as a reference shape for the specific session. This will allow using a separate reference shape element only at an initial calibration stage of the examination and not throughout the examination and optionally for each of the subject's eyes (as their size do not change over time) these values can be permanently stored for using in multiple eye examinations over time by the same subject.

According to some embodiments, the feedback module 113 is configured for outputting instructions to the user and also for allowing the user (which may be the subject himself/herself) to input feedback information such as for indicating that he/she has reached the MDBA distance according to his/her subjective view and for outputting the resulting refraction error (dioptric power) of the respective tested eye.

In some embodiments, a feedback mechanism for indicating that the subject has reached the MDBA, can include, for instance, identification of removal of the credit card or any other reference shape element (if using a video camera for instance) followed by an identification of two eyes located in the region of the reference shape prior to its removal, using the camera sensor and the processor unit.

According to some embodiments, the refractive error module 114 is configured to receive the measured MDBA and other measured data from the distance estimation and calibration module 112 and calculate the refracted error of the tested eye according to the MDBA value and the characteristics of the target presented at the time the MDBA related sensor parameter was measured. The resulting calculated refractive error of the tested eye is then outputted to the subject through the UI 111 (e.g. by using visual representation thereof over the display area 135). The resulting refractive error may also be transmitted upon user selection for ordering glasses through the internet (using communication means of the personal device) with the corrective lenses according to the examination results. In this case the UI 111 also includes an ordering platform for allowing the subject to place an order, select glasses frame and pay etc.

According to some embodiments, the results of the eye test of a measuring session may be sent to a third party alternatively or additionally to presenting the results to the subject.

Figure 3A:
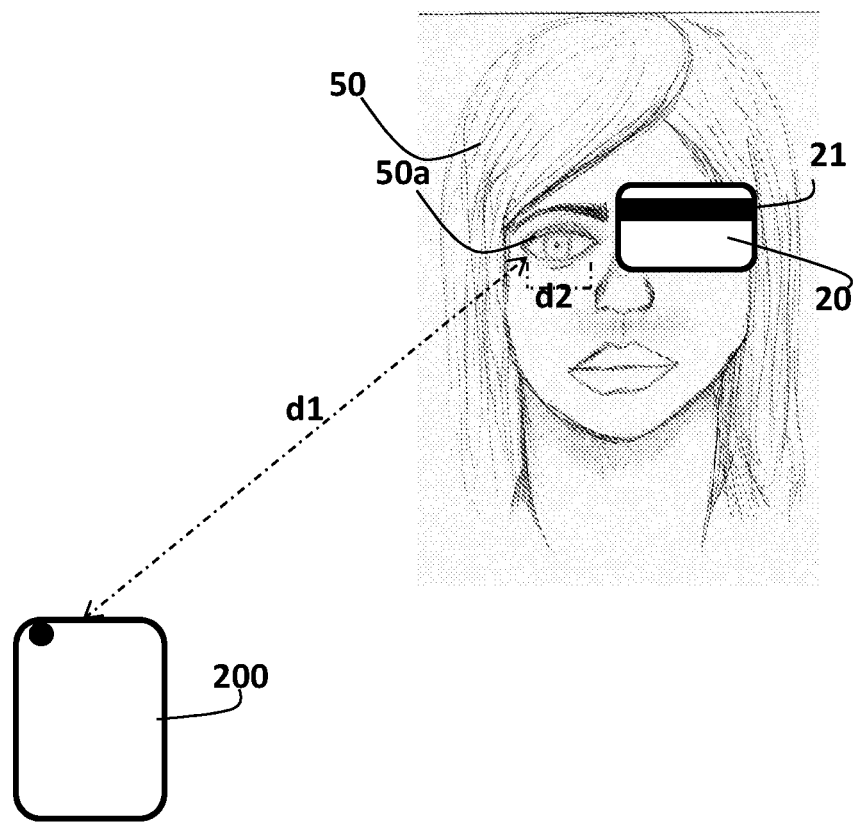
FIGS. 3A-3B show how the subject uses an integrated personal smartphone device operating a designated application for carrying out a self-examination of refractive error, using a camera as a sensor that allows measuring the distance between the subject's tested eye and target image presented thereto, according to some embodiments of the invention.
Figure 3B:
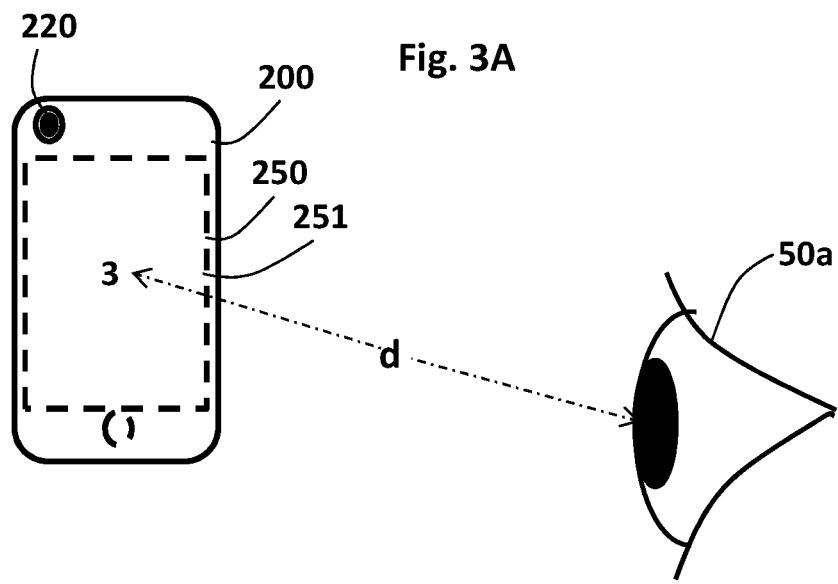

FIGS. 3A-3B show how the subject uses an integrated personal smartphone device 200 having the designated application operable therethrough for carrying out self-refractive error examination, according to some embodiments of the invention. The smartphone device 200 has a camera 220 and a touch-screen 250 embedded therein and typically also a microphone and a speaker for inputting and outputting audio data.

FIG. 3A shows how the calibration process is carried out by having a subject 50 holding a reference shape element 20 including a reference shape 21 of known dimensions over his/her untested eye covering thereof. The reference shape 21 is used to calculate the absolute width "d2" of the tested eye and optionally also the length thereof.

The user is asked (e.g. through audio means i.e. speaker of the smartphone) to hold or position the smartphone at the farthest position in which he/she still clearly identify the sign in a substantially good acuity and the camera 220 captures one or more 2D images of the tested eye once he/she indicates reaching that MDBA point or throughout the positioning including the time of indication. This allows the application to estimate the distance "d1" (see FIG. 3B) between the tested eye 50a and the presented target image at the time the subject has reached his/her MDBA and to calculate the refractive error thereby.

As mentioned above, various types of metering sensors may be used for deducing or directly measuring the distance from the tested eye to the target image that is displayed such as a camera (video and/or stills), 3D detectors, accelerator sensor, a proximity sensor, and the like. The algorithm used by the application to deduce the distance depends on the type of sensor used and the type and format of data outputted thereby. The following paragraph give out non limiting examples of how data from each sensor type can be handled to deduce the distance:

3D Sensor:

A 3D sensor maps an object Obj to a set of points $\{x_i, y_i, z_i\}$ in 3 dimension Cartesian coordinate (for instance using projected structures which form is distance dependent, distance form defocus, stereo-based triangulation, etc.). Hence, an eye (or any other facial shape) detection algorithm can be applied to detect an eye feature within the "Obj" and the distance from the eye to the target can be extracted as $d=\sqrt{(x_k-x_0)^2+(y_k-y_0)^2+(z_k-z_0)^2}$, where $\{x_0, y_0, z_0\}$ is the target location in the same Cartesian coordinate and k indicates a discrete point on the eye acquired by the 3D sensor.

Proximity Sensor:

A proximity sensor is a sensor able to detect the presence of nearby objects without any physical contact. A proximity sensor often emits an electromagnetic field or a beam of electromagnetic radiation (infrared, for instance), and looks for changes in the field or return signal. Use of the proximity sensor data in the nominal range can be applied to short distances distance measurement refinement, i.e. extending the accuracy of other method taken to evaluate the eye-target distance. The data from the proximity sensor could also be applied solely for distances in the nominal range. This sensor can directly measure distances outputting the distance between the sensor and the object it is directed to allowing deducing the distance between the tested eye and the target image by knowing the fixed location of the display area in relation to the sensor.

Accelerator:

An accelerator is a sensor that delivers acceleration data at a given time. The distance at any given moment can be calculated with the calculation unit after set of two conditions have been satisfied. To deduce the distance between the tested eye and the displayed target image, the data processing of the data from the accelerator may include a calibration procedure for initial eye-target distance—$x_0$.

A calibrated initial eye-target distance can be set to zero, while holding the smartphone closely to the eye and beginning the measurement. The subject holding the smartphone or any other device consisting accelerator sensor maintain a steady fixed location of the head, while allowing the accelerator device to move back and forward. The distance at any given moment can be calculated according to the following parameters:

$a_x(t)$ = acceleration data from acceleration sensor $x_0$ = calibrated initial eye – target distance $$v_x(t') = \int_0^{t'} a_x(t)dt$$

$$x(t') = \int_o^{t'} v_x(t)dt =$$

$$\int\int_0^{t'} a_x(t)dt = \int\int a_x(t)dt - \int\int a_x(0)dt = \int\int a_x(t)dt - x_0$$

In the same manner, the data from the accelerator sensor for $a_y(t)$ and $a_z(t)$ could be applied to evaluate y(t') and z(t'), where the displacement vector will be: $r(t')=\sqrt{x(t')^2+y(t')^2+z(t')^2}$ The use of the accelerator sensor can be applied solely or in conjunction with other distance metering sensors to increase the metering range, reliability and sensitivity.

Camera:

The estimation can also be conducted by a camera taking photos of a an element of a known size or that includes a reference 2D shape having a known size (dimensions wherein the length or size of an image of the reference shape or element allow deducing the distance at least between the camera and the element. A known element may be: (i) a credit card or any other card having a black strip in the back having known length and/or width; (ii) a coin or bill; (iii) pre-calibrated shapes such as eye size, distance eyes or any other facial feature of the subject.

The measurement is performed using devices consisting of a camera and a distance display unit, screen and/or projection unit and calculation unit (processor). The measurement can be carried out using a single device which consists of a camera unit and/or distance metering unit, display and/or projection unit and calculation unit (examples—smartphone, tablet, computer with camera, smartphone with integrated projector), or an assembly of separated devices, each one consisting at least of a single unique unit, that are connected to one another over a local connection (example: cables, WiFi, Bluetooth, infrared or any other wireless connection) and/or remote connection (for example: over IP).

The calibration is conducted by measuring the ratio of the feature size to a known element/reference shape size. The calibration procedure is performed with a camera positioned at a fixed distance from both the object feature and the calibrating object. The calibration object plane and the element's feature plane may not coincide. In such a case the offset between the planes should be taken into consideration in the distance evaluation process.

When using a camera sensor producing 2D images data, the camera $$\frac{efl}{pitch}$$

ratio should be given or calibrated, where "efl" is the camera effective focal length and "pitch" is the sensor effective pitch. The effective pitch is the physical distance between adjacent pixels multiplied by the down-sampling.

h=known Obj height
h'=image of known Obj height
u=distance between camera lens to known Obj
v=distance from camera lens to sensor
efl=effective focal length of the camera h'_pixles_estimated=pixels count of estimated known Obj height
From triangles similarity:

$$\frac{h\prime}{h} = \frac{v}{u} \cong \frac{efl}{u}$$

$$h' = \text{pitch} * h'\_\text{pixels\_estimated}$$

$$u_h \cong \frac{efl * h}{h\prime} = \frac{efl}{\text{pitch}} * \frac{h}{h\prime\_\text{pixels\_estimated}}$$

$$u_w \cong \frac{efl * w}{w\prime} = \frac{efl}{\text{pitch}} * \frac{w}{w\prime\_\text{pixels\_estimated}}$$

Several methods can be combined/used in parallel in order to increase accuracy estimation of $u=f(u_h, u_w)$. A calibration procedure for $$\frac{efl}{\text{pitch}}$$

can be done using a known object size imaged by the camera from a known distance.

Distance estimation precision:

$$M = \frac{v}{u} \cong \frac{efl}{u}; h'' = (h + \Delta h) * M.$$

$\Delta h$ is the length estimation error in object plane;

$$u' = \frac{h * efl}{h''} = \frac{h * efl}{(h + \Delta h) * M},$$

where u' is the estimation of the true "u":

$$u' = \frac{h * efl * u}{(h + \Delta h) * efl} = \frac{h * u}{h + \Delta h}$$

$$u = mdba$$

$$P' = \frac{1}{u'} = \frac{h + \Delta h}{h * u} = P + \frac{\Delta h}{h * u} \triangleq P + \Delta P$$

$$\Delta P \triangleq \frac{\Delta h}{h * u} = \frac{1}{h * u} * \frac{\Delta h\prime}{M} = \frac{\text{pixels\_error} * \text{pitch}}{h * u} * \frac{u}{efl} = \frac{\text{pixel\_error} * \text{pitch}}{h * efl}$$

For a standard camera lens efl of 3 mm, sensor pitch of 1.4 μm (iPhone 5, Samsung Galaxy S3) and a credit card set as known Obj, pixels_error of 45[pixels] is allowed to enable 0.25 D precision.

The refractive error measuring may include measuring at least one of the following parameters: spherical equivalent power (SEP) and/or astigmatism power; and (iii) astigmatism axis or angle. The examination can involve monocular and optionally also binocular exams.

According to some embodiments of the invention, the target images used for testing refractive error of the eye including spherical and cylindrical errors may vary depending on the particular error tested. For instance, "single-directional" target images may be used to test and quantify astigmatic errors. The tests include specific known signs such as letter and numbers (optotypes) of known font, size, color, texture background. This will provide the dioptric power of the tested eye. Other target images for testing visual acuity including cylindrical error may have "multi-directional" or "omnidirectional" symmetries such as concentric rings shapes, sun shapes or papillon shapes. When using multi-directional or omnidirectional target images the MDBA may be measured by requiring the subject to view a specific visual effect at maximal distance from the target image for determining far cylindrical power, near cylindrical power and cylindrical angle/axis of the tested eye.

The Target Image:

The target image presentation may include changing characteristics such as its size, color, pattern therein of the target image over time:

Target Size:

the size of the one or more signs of the target image (shortly referred to also as "the size of the target") may be calculated according to the following parameters/constants (Log MAR=Logarithm for the Minimum Angle of Resolution):

"offset" = distance between the tested eye and the reference shape

"dObjTarget" = distance between the target image and the reference shape

"d11" = distance between the tested eye and target image

"d12" = $dObjTarget$ + offset[m]

"RefdistanceLogMAR" = 1.2[LogMAR]

"Refdistance" = 6.3[m]

"RefTargetSize" = 8.7[mm]

"RequireLogMar" = required visual acuity

"fontConst" = fixed font size factor

"distanceCalibrateToRequiredLogmar" = $d12 * 10 \wedge \text{RequireLogMar}$ $$\text{TargetSize} = \frac{\text{DistanceCalibrateToRequiredLogmar}}{\text{RefDistance}} * \text{RefTargetSize}$$

$$\text{FontTargetSize} = \text{FontConst} * \text{TargetSize}$$

Dynamic Target Size:

Target with size preserving a constant viewing angle along all axial locations. The value d12 is constantly updated by the processor (e.g. by the distance estimation and calibration module) as the distance between the eye and the target changes. Consequently, FontTargetSize (0095) follows the change in eye-target distance and maintains a constant viewing angle of the target for a specified required visual acuity Fixed size targets: In these cases the size of the target image presented at a certain "trial$_i$" is adjusted to the required visual acuity at distances matching the MDBA of previous trial (trial$_{i-1}$) in the session. The value d12 used in the algorithm is kept constant throughout the session and does not correspond to the real time eye-target distance change. For example, if the MDBA resulting from a previous trial was 33 cm, a calculation using d12=0.33 [m] will be used to conclude the target size throughout this trial, in spite of the real time changing distance between the target and the eye.

Sign shapes in the target image may be, for example, letters, numbers, ring shapes connected to one another or concentrically positioned in one another in a predefined order (e.g. multiple concentric rings having a predefined space separating each pair of adjacent rings).

One Dimensional Target:

$f$ = spatial frequency $\theta$ = angle of desired one dimentional target $A$ = Constant $$z(x, y) = \frac{A}{2}(1 + \cos(f*x*\cos(\theta) + f*y*\sin(\theta)))$$

Spatial frequency of the one dimensional target "f" should meet the required visual acuity.

Meaningful One Dimensional Target:

The body of the meaningful target is made up of one dimensional target such as lines in a certain orientation. One embodiment of meaningful target can be letters such as targets 22a-22e shown in FIG. 4A-4E. Another embodiment can be a known simple or complex shape such as an animal. The purpose of this target is to enable the subject a meaningful identification of details of the target image.

Figure 4A:
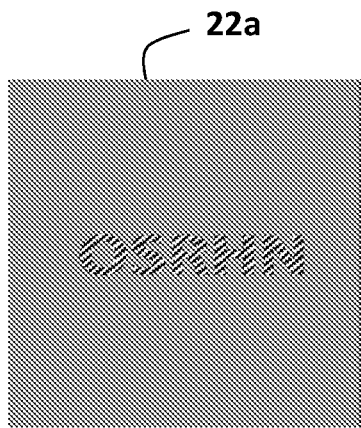
FIGS. 4A-4L show different types of target images that can be used for the examination, according to embodiments of the invention.
Figure 4B:
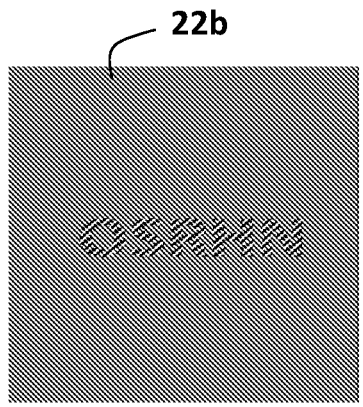
Figure 4C:
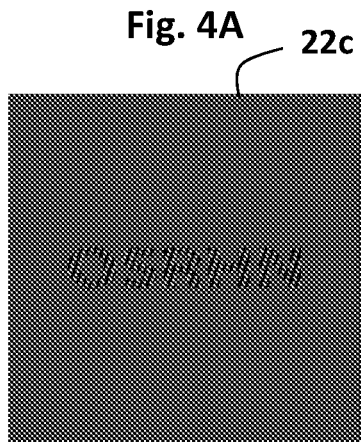
Figure 4D:
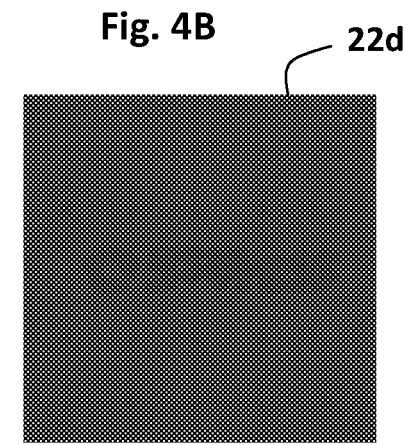

At a longer distance than the MDBA, where the subject perceives a blurred image, the one dimensional target translates into pattern-less average of the colors consisting the one dimensional peaks (FIG. 4D). The background is tuned to that blurred average color. In this case, the blurred image ends up in an almost unperceivable image. Only when viewed at distance closer than the MDBA, the one dimensional target becomes apparent, hence the letters or shapes mask become perceivable and meaningful (FIG. 4C).

Angle of desired one dimensional target corresponds to the subject's angle of astigmatic error.

Background color of the displayed sign(s) in the target image should preferably allow a defocused image to be almost not perceivable. A guideline for background intensity is 0.67, where the constant A used in [00186] is 1.

Figure 4E:
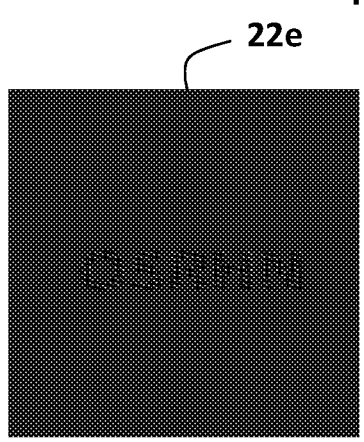
Figure 4F:
Figure 4G:
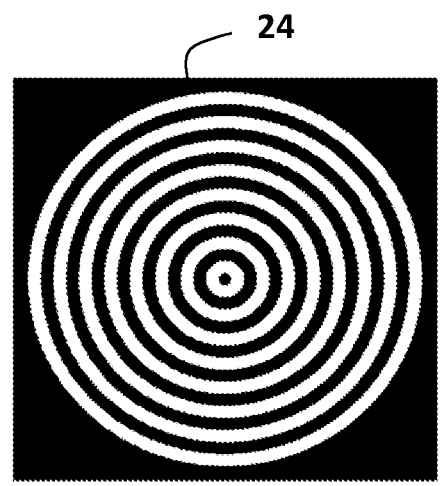

FIG. 4F shows target image 23 showing a specific order of optotypes for testing the sphere equivalent power (SEP). FIG. 4G shows a black and white (BW) target image 24 of white concentric rings over a black background for testing cylindrical error (i.e. angle and power of cylinder).

Figure 4H:
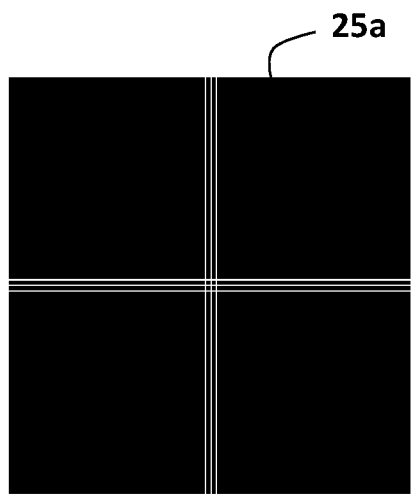
Figure 4I:
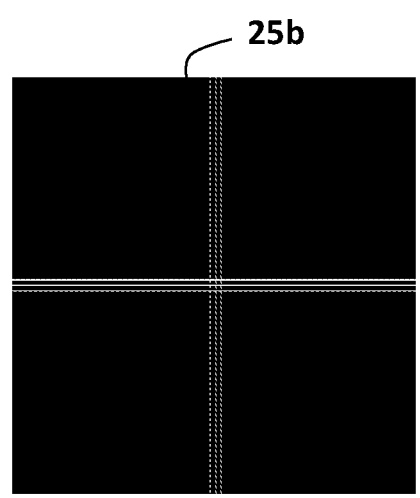

Cross target images such as target images 25a and 25b shown in FIGS. 4H-4I show a cross made up from two or more lines at a certain angle 'θ', each one with a width of w displaced one from another at a width of 2·w and two or more lines, at an angle of θ+90 each one with a width of w displaced one from another at a width of 2·w The cross could be oriented to any given angle.

Target color: The color of the target or some features thereof (e.g. its background the color of the signs therein, the contrast level of colors of the stripes in a pattern in the sign(s) thereof and the like) and/or changing thereof during the examination can be used to fine tune the MDBA and/or assist at locating any cylindrical aberration (astigmatism) of the eye and determining the cylindrical aberration angle.

Virtual chromatic cross cylinder target image such as image 25b (FIG. 4I): A cross target image having the color of the lines at angle θ set to Green and setting the color of the orthogonal lines to Red. According to some embodiments this target image can be rotated during examination for measuring astigmatism to an angle of θ+90.

In the case where a black on white image has fallen on the retina, the Red image would be imaged behind the retina by approximately 0.25 D. The corresponding Green image results in an axial displacement of the image in front of the retina by approximately 0.25 D. This chromatic method can be used in conjunction with the virtual chromatic cross cylinder shifts a one dimensional target in front of the retina and its corresponding orthogonal one dimensional target behind the retina. The described method corresponds to what a traditional cross-cylinder would have done. The dioptric power of the virtual chromatic cross-cylinder would be determined by the screen spectral response. The longer excitation wavelength of the red will result in an effectively higher dioptric power of the virtual chromatic cross-cylinder. Furthermore, a use of the shorter wavelengths, such as the blue or purple, could be used in conjunction with red to increase the dioptric power to +−0.5 D, since the chromatic aberration for blue wavelength (~480 nm) is −0.75 D and for red (~636 nm) is +0.25 D. In this case, however, an offset of −0.25 D to the yellow as the middle should be taken under consideration and the target should be presented at a distance closer by 0.25 D than the estimated sphere equivalent. For example, if MDBA of 33.3 cm was estimated, corresponding to −3D of sphere error, the use of blue-red virtual chromatic cross-cylinder should be used in 0.308[m] from the user's eye.

Chromatic meaningful one dimensional target images 22b, 22c and 22e (FIGS. 4B, 4C, 4E): In this method, the color of the meaningful one dimensional target is Red color (FIG. 4C) and the pattern stripes are set at a certain angle θ. The perceivable image is compared to setting a Green or Blue color to the meaningful one dimensional target at the same angle. This is repeated at an angle of θ+90 (FIG. 4E). This method applies the same principle of virtual chromatic cross cylinder, where in this method the one dimensional target is used in order to enable recognition of figures or letters.

Another optional method is to use a meaningful target image with a combination of letters. Each letter may differ in color, orientation, pattern and/or texture.

Figure 4J:
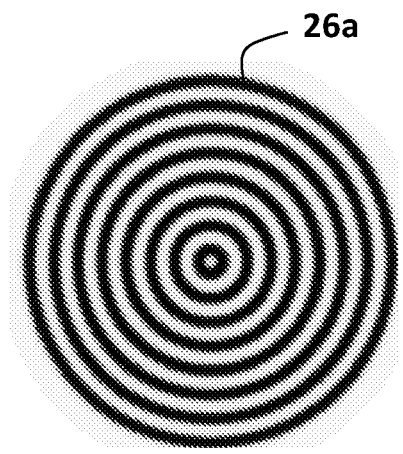
Figure 4K:
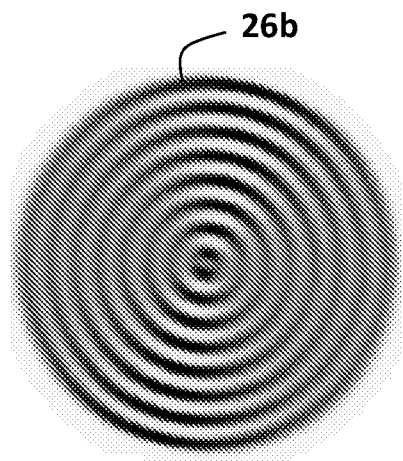
Figure 4L:
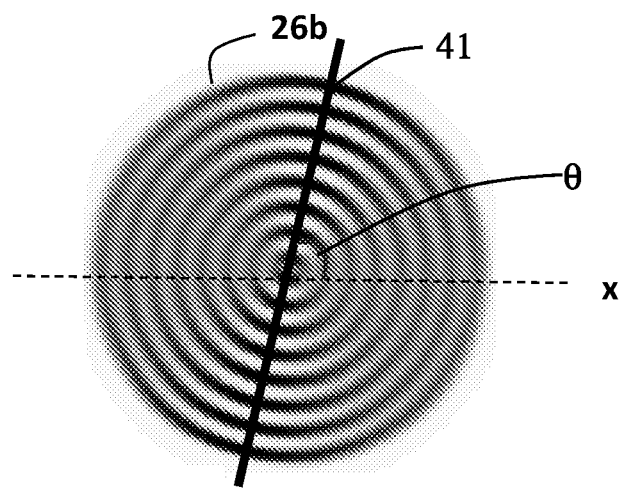

FIGS. 4J-4L show a black and white (BW) target image 26a-26b with concentric rings: FIG. 4J shows the image 26a as displayed over the screen, where FIGS. 4K and 4L show an image 26b illustrating how the image 26a will be perceived by a subject having an astigmatism.

Figure 5:
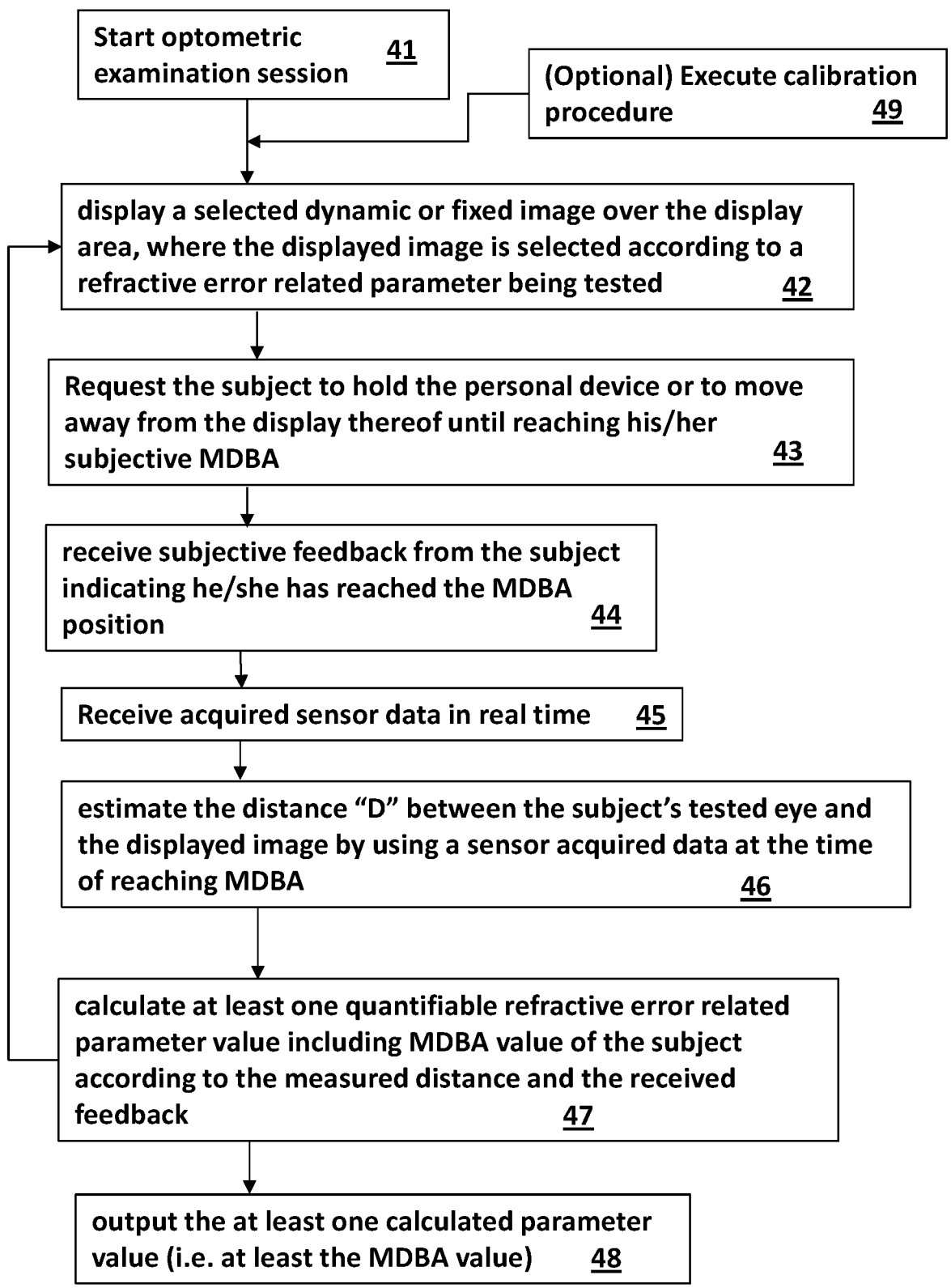
FIG. 5 shows a flowchart illustrating a process for measuring refractive error of a subject's eye, according to some embodiments of the invention.

Reference is now made to FIG. 5, which is a flowchart schematically illustrating a process for measuring refractive error of a subject's eye, according to some embodiments of the invention. The process includes initiating an examination session 41 (also shortly referred to as "session") e.g. through GUI of the designated application operable through the subject's personal device. Once the session is initiated a target image, having preselected graphical characteristics is displayed over the display area (e.g. over the screen of the personal device) 42. The subject/user may be enabled to select the type of refractive error he/she desires to check at each point or the application may be set to check all types at a predefined order by displaying target images selected accordingly.

The subject, wearing no refractive correction means, is then requested by the UI of the application to establish what he/she thinks is the MDBA 43 in respect to the presented image and indicate 44 when reaching this MDBA position through feedback option(s) of the application and UI thereof. The subject can look for the MDBA position either by physically moving away from the display area or by distancing the display area itself. The instructions can be given, for example, by outputting audio and/or text messages via the screen and/or the speaker of the personal device, respectively.

The sensor of the system/personal device may be operated by the application such that in continuously or repeatedly acquires data or only upon input of the subject/user approving thereof once reaching the MDBA. In any case the application is set to identify or synchronize the moment in time in which it receives indication from the subject that he/she has reached the MDBA location and the acquired data of the sensor at that time. The acquired sensor data is received at the processor of the system 45 and may also optionally stored in a designated storage unit.

The received acquired data (e.g. the image of the tested eye or another reference shape) may then be processed to estimate thereby (deduce therefrom) the actual distance "D" between the tested eye and the target image at the time of reaching MDBA 46.

According to some embodiments, as mentioned above, in case of a sensor that provides 2D images and when a reference shape of known dimensions is used, the size of one or more dimensions (e.g. width and/or length) of the image of the reference shape is compared to the absolute corresponding dimension(s) thereof to deduce a distance "D1" between the sensor and reference shape position and then the distance "D" between the tested eye and the target image is deduced from: "D1" by having the real (absolute) distance between the display area and the sensor and the distance between the reference shape and the tested eye known.

The estimated distance "D" between the tested eye and the target image and the known characteristics of the target image are then used for calculating value of one or more parameters associated with the refractive error of the eye 47 such as the power "P" as mentioned above. The resulting value(s) may then be outputted to the subject 48 e.g. by presenting them over the display area and/or outputting an audio message.

According to some embodiments, the examination may further include a preliminary calibration process 49 in cases in which the sensor has to be calibrated in respect to a specific reference shape dimensions of which are not known in the system. For example, in cases in which a known temporary reference shape (such as a credit card magnetic stripe) is only used for calibrating the size of the tested eye of the subject also used as a reference shape through the actual measurements session.

Figure 6:
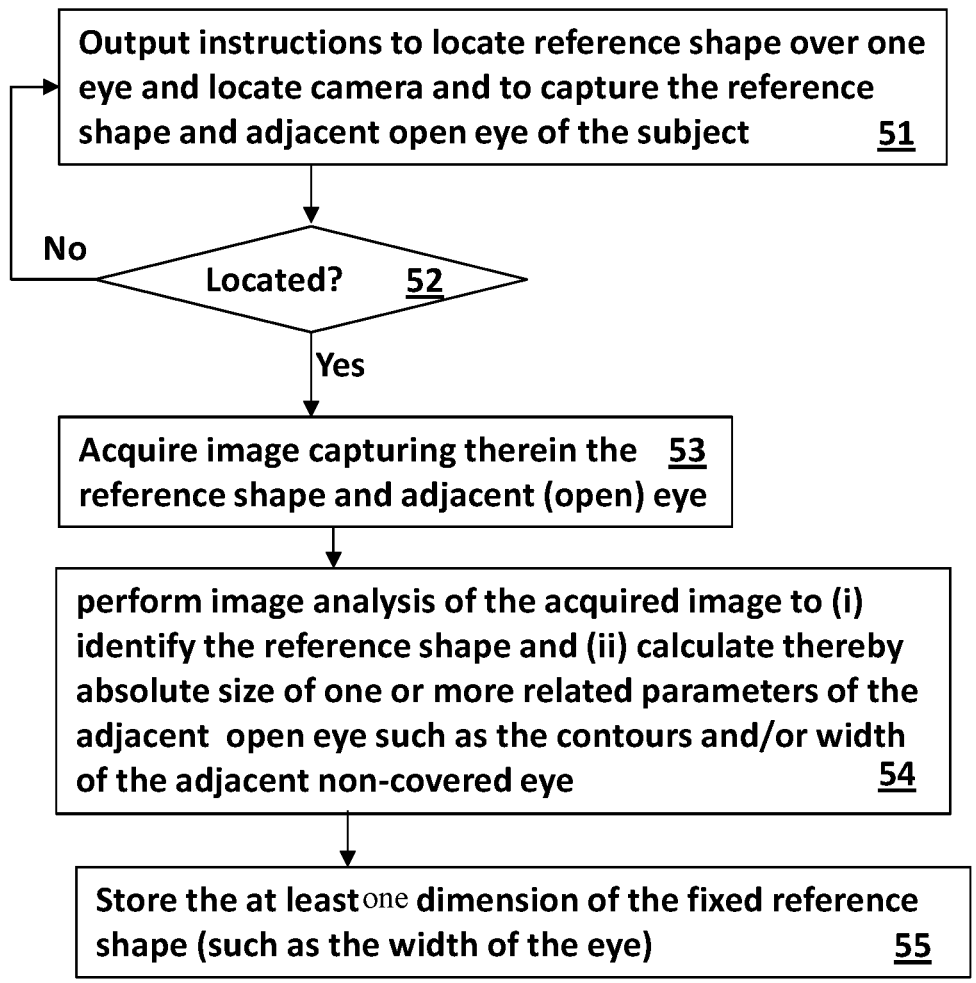
FIG. 6 shows a flowchart illustrating a preliminary calibration process for measuring a permanent reference shape by using a temporary reference shape, according to some embodiments of the invention.

FIG. 6 shows a flowchart illustrating a preliminary calibration process for measuring a measurement reference shape by using a temporary reference shape, according to some embodiments of the invention, in which the sensor used, is a camera capable of producing 2D images data. The application may be configured for outputting an instruction to the subject requesting him/her to hold a known temporary reference shape element such as a credit card in a specific position (e.g. covering the untested eye with the magnetic stripe shown) 51. Once the temporary reference shape element is positioned 52 the subject can indicate it through a special UI input platform or simply operate the camera through the UI for acquiring an image 53 the acquired image must include both the entire reference shape element and the tested eye. The acquired image data is then processed by carrying out an image analysis thereof 54 a process which may include, for example: (i) identifying the dimension(s) of the temporary reference shape (e.g. width and/or length and/or angular positioning of the magnetic stripe) producing one or more ratio scales such as width and/or length scales; (ii) identifying contours of the fixed reference shape (e.g. identifying the contours of the tested eye); and (iii) measuring one or more absolute value of one or more parameters of the fixed reference shape (such as the absolute length of the eye). The absolute value(s) of the respective parameter(s) may then be stored at the system memory unit 55 for using thereof for distance metering.

Figure 7:
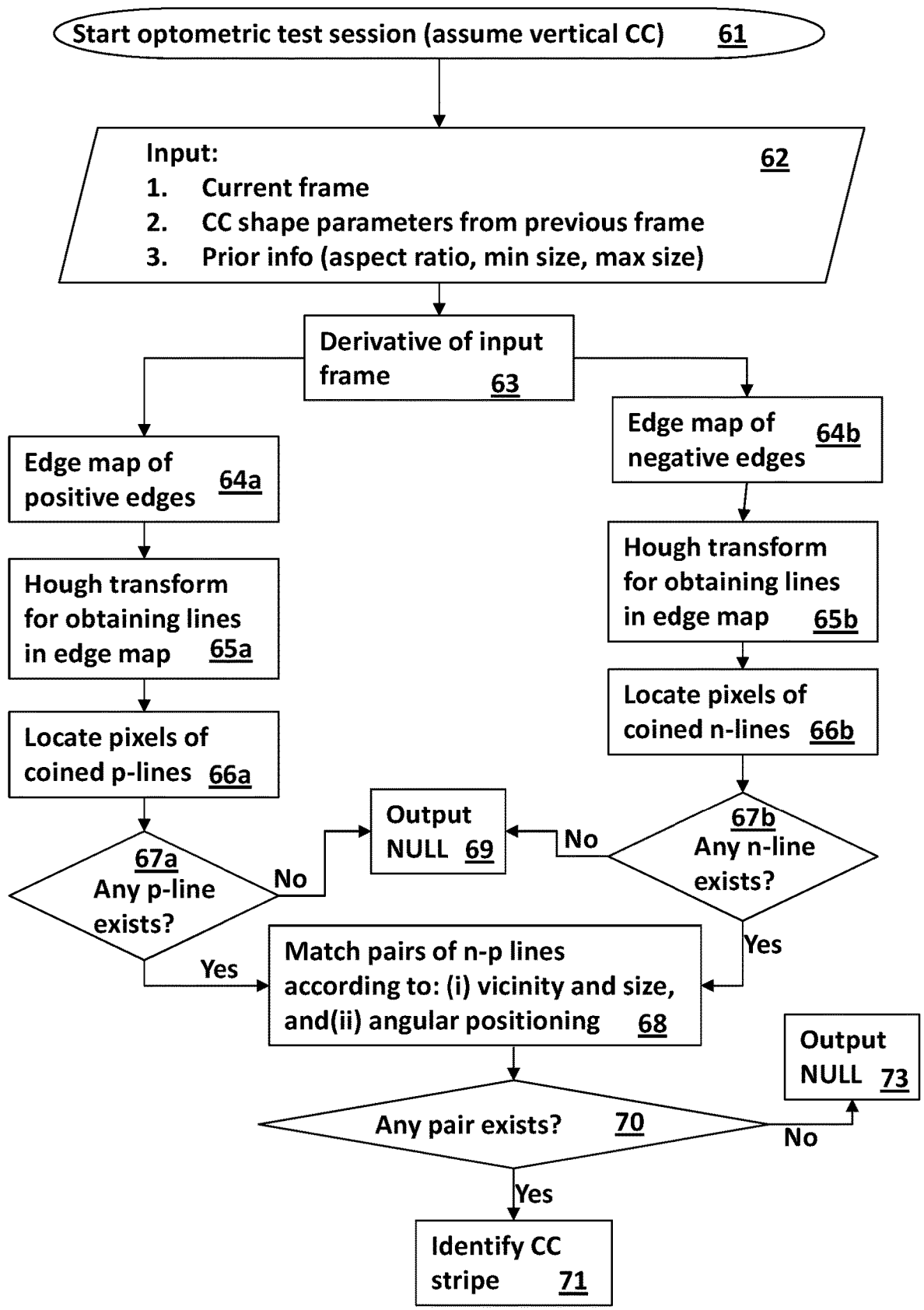
FIG. 7 shows a flowchart illustrating a process for measuring for identifying a reference shape of a magnetic stripe of a credit card through acquisition of 2D images thereof for distance metering, according to some embodiments of the invention.

FIG. 7 shows a flowchart illustrating a process for repeatedly identifying a reference shape of a magnetic stripe of a credit card held by a subject in a manner that the card covers his/her untested eye, through acquisition of 2D images thereof for the purpose of distance metering, according to some embodiments of the invention. Once an examination is initiated 61 one of the application's modules receives input data 62 including a 2D image of the currently captured frame, the dimensions of the entire credit card (CC) element and uses the input data 63 for carrying out two processes parallel to identify the vertical and horizontal proportions of the image of the CC. To identify the length of the image of the magnetic stripe (in number of pixels) the algorithm finds the edges thereof 64a/64b and identifies size of longitudinal and horizontal ('n' and 'p') lines that stretch from one edge of the magnetic stripe to another in pixels by using Hough transform 65a-66a/65b-66b and matches perpendicular 'n'-'p' lines according to vicinity, size, level of perpendicularity and the like 67a, 67b, 68-69. The n-p pairs are then used for estimating the vertical and horizontal dimensions of the magnetic stripe image 70-71 e.g. by averaging all the pairs' p lengths and n lengths (separately).

The systems and methods of the present invention, in some embodiments, may be configured to first carry out examination of myopia/hyperopia/presbyopia by using a first set of target images and then carry out a test for measuring astigmatism by measuring cylindrical angle followed by measuring the cylindrical power.

The cylindrical angle, if exists, can be estimated by pointing the subject to a strict range of distances concluded from spherical MDBA (MDBA related to a target with no profound directional preferences). The subject is guided to start viewing a concentric symmetrical target such as a dual colored image (one color for the ring and one color for the background such as black and white (BW) concentric rings shape (see FIG. 4J) at a distance MDBA, where all concentric rings appear equally sharp. Then the subject is encouraged by the UI to locate a sandglass image (also called hourglass or papillon), if exists, further than the MDBA but no farther than 2*MDBA. This strict range of distances assures identification of cylindrical power up to half of the sphere equivalent power. Receiving a subjective feedback about asymmetrical perception (FIG. 4K) of a symmetrical target (FIG. 4J) (such as a circle or concentric rings such as shown in FIGS. 4G and 4J-4L) and the angle (FIG. 4L) in which the asymmetric perception occurs allows calculating astigmatism power and axis. From the location where the hourglass is mostly evident, where at a certain angle there is an hourglass with sharp high contrast arcs and a perpendicular blurred wider hourglass, the axis can be estimated as well as the cylindrical power. The subject is guided to locate a bar such as bar 41 in FIG. 4L at the middle of the sharp hourglass for determining the angle "θ" between a horizontal axis "x" of the image and the bar 41 for calculating the astigmatism angle. The distance of the eye-target, in which the sharp hourglass is observed corresponds to the power of the weak axis of the cylindrical error. Verification to the astigmatic power can be aided by one dimensional target at the angle found. The same strict range of distances is advised to avoid contrast reversal of the periodic target.

According to some embodiments, the astigmatic angle is determined by using one or more of the following methods:

The Achromatic Method:

According to this method, the subject is required to look at a BW target image with details indicating the orientation of astigmatism (for example—concentric equally spaced rings). The subject is instructed to view the target at a distance slightly farther than the MDBA. The subject indicates the orientation by means of a subjective response (feedback) through the device's/system's input means. In the case of concentric circles the subject indicates the orientation of the higher contrast area.

The Chromatic Method:

According to this method, the subject is required to look at a chromatic target with details indicating the orientation of astigmatism such as the virtual chromatic cross-cylinder. The subject is directed to view the target at a specific distance and/or distance range. The chromaticity difference/contrast enables for an easier location of the astigmatism axis.

Determining the Astigmatic Power:

The targets used for this type of astigmatism measurements are one-dimensional targets at the astigmatic meridian. These targets help evaluating the MDBA for that astigmatic power. The concentric rings image (FIG. 4H) may also be used until the most distinct hourglass image is formed by the high and low contrast areas of the concentric rings. The astigmatic target is moved backwards and forwards to the point of greatest appreciable sharpness indicated by the subject and taken as the actual distance "D" of the MDBA thereof.

The subject is directed to view the target at a distance farther than the sphere equivalent MDBA. For a certain maximum astigmatic error, the target distance should be in the range of:

$$\left[ SEP\_mdba, \frac{1}{\mathrm{abs}(SEP) - 0.5 * \mathrm{abs}(\mathrm{maximum\_ASTG\_error})} \right].$$

For example: for SEP of −2.50 D, the MDBA is 400 mm; for a maximum ASTG_error of −3.00 D the range for the presented target should be between 0.4 m to 1 m.

For fine tuning various chromatic targets can be used. The reference shape element used for distance metering (example: credit card) may be used as an occluding means while the examination of the un-occluded eye takes place.

For testing lower diopter: SEP<1.50 D the test is done with auxiliary means such as a mirror. In this method the screen should face the mirror and the back camera facing the subject. The observed image distance by the subject is now the distance between the subject and the rear camera plus twice the distance between the screen to the mirror. This way the subject can still hold the smartphone in reasonable distance (~65 cm) while viewing targets at distances up to 6 m. In this method the rear camera can be used to estimate the eye-rear camera distance, while the front camera can estimate the front camera—mirror distance. In the later example, the smartphone known shape could be used as known object size to deduce distance.

FIGS. 8A-8D show a target image 27a for measuring axis of astigmatism using the chromatic method: FIG. 8A shows a colored stripes target image 27a for astigmatism measurements that includes three vertical parallel lines the middle one is green and the two outer lines are red, over a black background, where the lines are separated from one another at a known separation difference; FIG. 8B shows an image 27b indicating how the target image 27a will be perceived by a subject having angle of astigmatism of 0°; FIG. 8C shows an image 27c indicating how the target image 27a of FIG. 8A will be perceived by a subject having angle of astigmatism of 45°; and FIG. 8D shows an image 27d indicating how the target of FIG. 8A will be perceived by a subject having astigmatism that is co-aligned with the direction of the presented colored stripes;

When the target image 27a of FIG. 8A is viewed by a subject having astigmatism refractive error a certain color blending can occur. For example, where green blur overlaps on red blur, a yellow line is created. It is shown in FIG. 8D that minimal color blending (yellow color generation) occurs when astigmatic axis is co-aligned with stripe direction. This test is to recognize when these two axes are co-aligned.

Figure 9A:
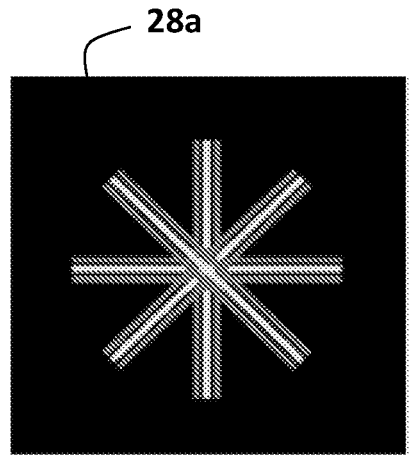
FIGS. 9A-9C show a target for measuring axis of astigmatism using a chromatic method.
Figure 9B:
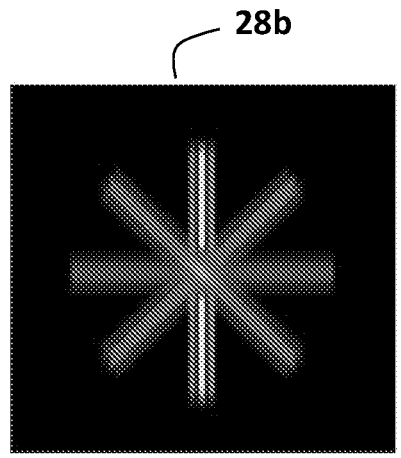
Figure 9C:
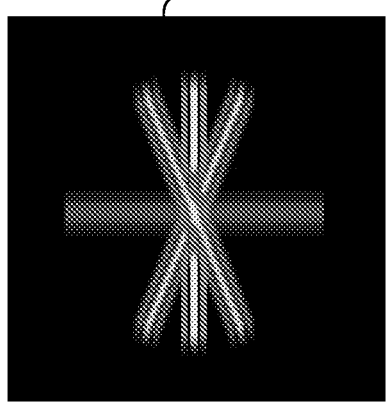

FIGS. 9A-9C show another target image 28a for measuring axis of astigmatism using the chromatic method: FIG. 9A shows a target image 28a with multiple colored stripes sets for astigmatism measurements that includes four sets of stripes each set includes three parallel red-green-red stripes separated equally distance separated, where the sets of stripes angularly cross one another such that the angle between each adjacent pair of stripes-sets is substantially equal; FIG. 9B shows an image 28b illustrating how the target image of FIG. 9A will be perceived by a subject having astigmatism at an angle that is close to $\alpha_1$=0°; and FIG. 9C shows an image 28c illustrating how a change made to the target image 28a of FIG. 9A according to feedback of the subject indicating that the sharpest stripes set he/she perceive is as shown in FIG. 9B.

According to some embodiments, to accurately measure the angle of astigmatism of the subject, the first target shown to the subject is a colored symmetrical image displayed at MDBA such as the target image shown FIG. 9A. Once FIG. 9A is displayed at the MDBA, the subject is encouraged to distant the target to a location where one or more sets of strips are sharper than others and then required to provide feedback indicating which of the four stripes-sets is seen as the sharpest. In this example, FIG. 9B represents a situation in which the specific subjects views the vertical set of stripes as the sharpest. The feedback of the subject will then initiate a refinement process in which, for example, the other non-perpendicular stripes-sets will be angularly moved such that they will have a smaller angle between them and the selected sharpest stripes—set as shown in FIG. 9C. If two sets were identified as equally sharp, the target will rotate to locate the main cross in the middle of the identified two sets. The subject is asked to provide feedback again indicating now which one of the stripes-sets is the sharpest to refine the angular astigmatism. This process of bringing the adjacent stripes-sets closer to the selected sharpest set can be repeated until the stripes-set selected is the same as the previously selected one. Alternatively, a refinement process to the angle may take place as a change of the angle of the entire target, using the UI and/or related sensors (i.e. camera identifying a tilt to the credit card, smartphone gyroscope sensor and the like) to locate the angle in which one of the sets is mostly sharp while the perpendicular set is mostly blurred.

Figure 10:
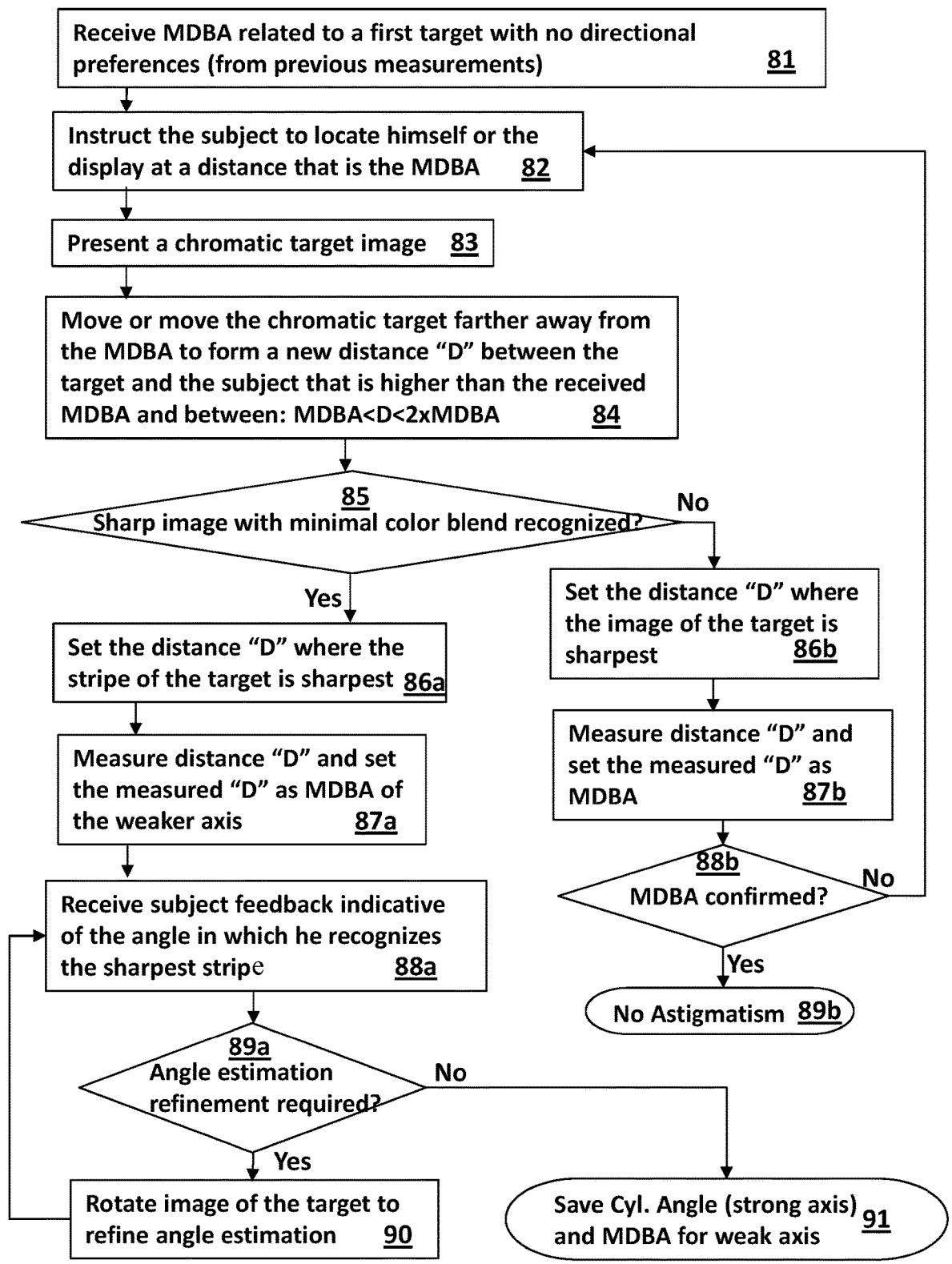
FIG. 10 is a flowchart, schematically illustrating a process for measuring cylindrical angle using a chromatic method, according to some embodiments of the invention.

FIG. 10 is a flowchart, schematically illustrating a process for measuring cylindrical angle using a chromatic method, according to some embodiments of the invention. This process includes receiving MDBA related to a previously measured MDBA when using a target with no directional preferences 81 and instructing the subject to locate the target image (by locating the display area) or the subject at the MDBA distance 82. Once the subject reaches the MDBA of the non-directional target, another target image is presented to him/her 83 through the display means showing chromatic target such as the stripes target shown in FIG. 9A for example and relocate the target or him/herself for reaching a new distance "D" between the target and the subject's tested eye within a range of MDBA<D<2×MDBA 84. The subject is instructed to find a distance in which he/she recognizes a one or more sets of stripes within the target that are sharper than others with minimum color blend 85 and set the distance at that location 86a if such recognition is made within the range. The system then automatically measures the distance "D" at that location 87b and set this distance as the new MDBA of the weaker axis. Subject's feedback indicating the angle of the sharpest stripe is received from the subject 88a and if no refinement of this angle is required 89a then the cylinder angle and MDBA of the weaker axis are saved 91. If a refinement of that angle is required 89a then the target image is rotated by the application 90 and steps 88a-91 are repeated.

In another embodiment, using the gyroscope sensor of the device, a change to the angle of the device will correspond to a change of the angle of the entire target. This can be applied to refine the angle using target 9A for example.

In case in which there is no recognition of a sharp image with minimal color blend within the range of MDBA<D<2×MDBA according to condition 85, the distance "D" is set where the image of the target is sharpest 86b and D is measured by the system 87b and set as the MDBA upon confirmation thereof 88b a state of "no astigmatism" is identified 89b.

Figure 11:
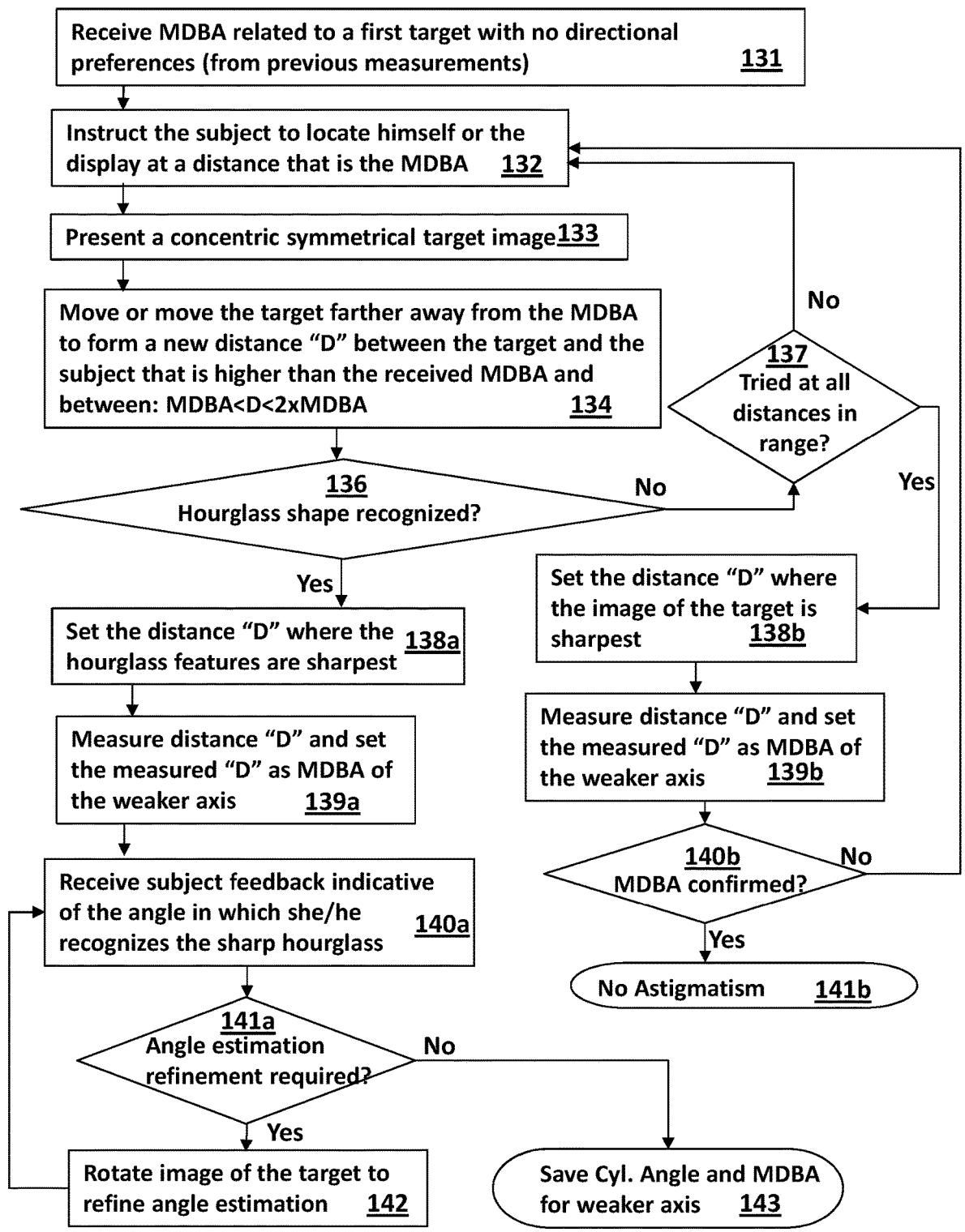
FIG. 11 is a flowchart, schematically illustrating a process for measuring cylindrical angle using an achromatic method, using a concentric rings target, according to some embodiments of the invention.

FIG. 11 is a flowchart, schematically illustrating a process for measuring cylindrical angle using an achromatic method, using a concentric symmetrical target, according to some embodiments of the invention. This process includes receiving MDBA related to a previously measured MDBA when using a target with no directional preferences 131 and instructing the subject to locate the target image (by locating the display area) or the subject at the MDBA distance 132. Once the subject reaches the MDBA of the non-directional target, another target image is presented to him/her 133 through the display means showing a concentric symmetrical image 26a such as the concentric rings image shown in FIG. 4J for example and relocate the target or him/herself for reaching a new distance "D" between the target and the subject's tested eye within a range of MDBA<D<2×MDBA 134 where the target is perceived as an hourglass. Once an hourglass image is recognized 136 the subject is instructed find the distance "D" in which the hourglass image is the sharpest, within the mentioned range 138a where this distance is measured and set as the MDBA of the weaker axis 139a. The subject may then input feedback indicative of the angle of the sharpest hourglass view 140 and then the cylinder angle of the strong axis and MDBA of the weak axis are saved 143.

Figure 12:
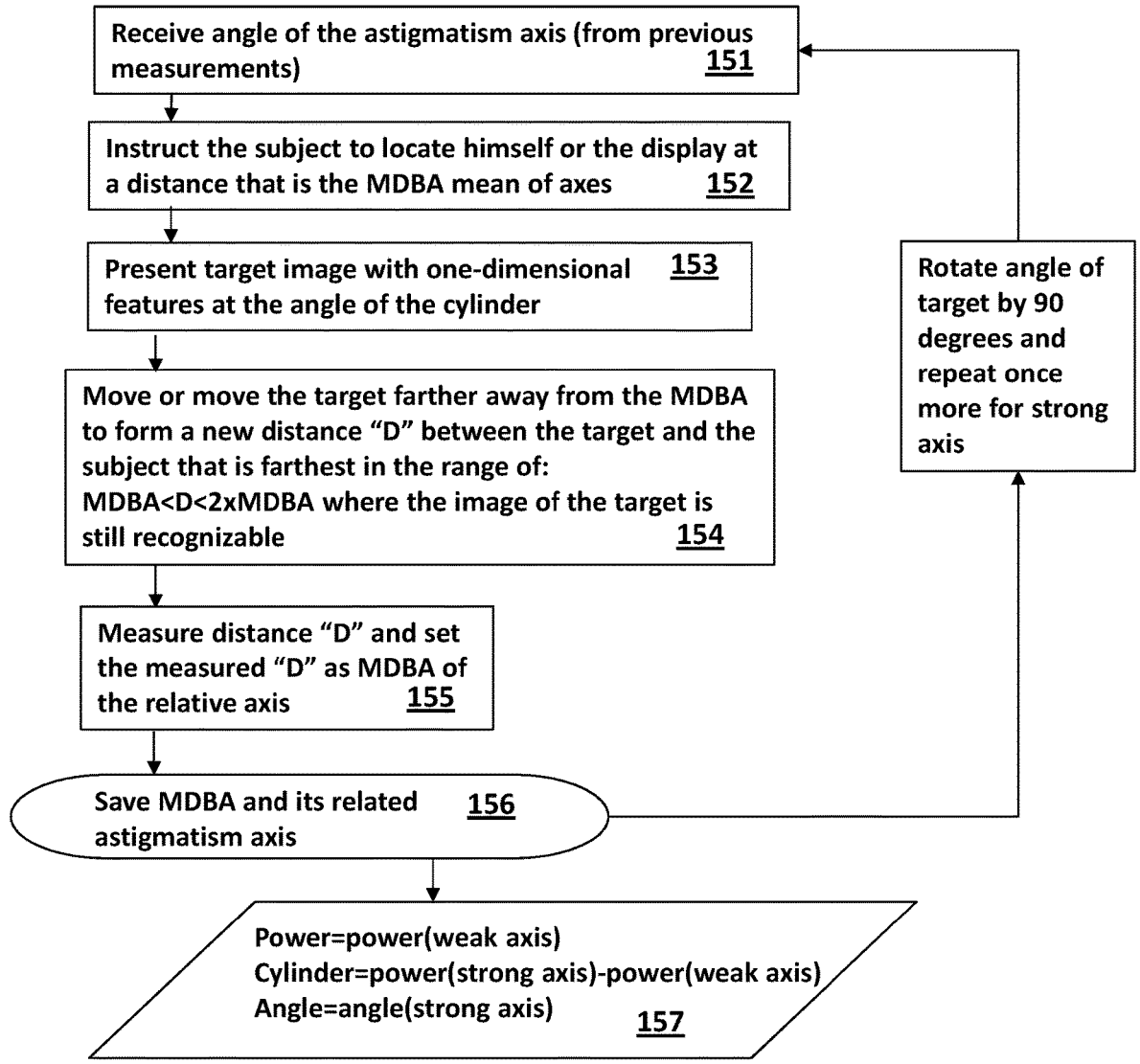
FIG. 12 is a flowchart, schematically illustrating a process for cylindrical power estimation using a target containing one dimensional features, according to some embodiments of the invention.

FIG. 12 is a flowchart, schematically illustrating a process for cylindrical power estimation using a target containing one-dimensional features, according to some embodiments of the invention. In this process, angle of cylinder axis is received from previous measurements 151 (e.g. resulting from process as described in FIG. 10 or FIG. 11). Then the subject is instructed to locate the display area (e.g. the screen) or him/herself so that the distance there between is the MDBA mean of axes 152. Once reaching this distance, a target image with one-dimensional features is presented at the angle of cylinder 153 and the subject is requested to increase the distance between his/her tested eye and the target to the most distant location (either by moving him/herself or by moving the display area farther away) within a range of MDBA<D<2×MDBA 154 where the target image is still recognizable. This distance is measured and set as the MDBA of the related axis 155 and these parameters are saved 156. To increase accuracy, one may repeat the process of cylinder power estimation at the orientation of 90 degrees to the previous measurement in order to locate the power of the strong axis. The final results allow to take these values for preparing glasses or contact lenses thereby 157. For example, the parameters include the following detailing: (i) power=power of the weak axis; (ii) cylinder=the difference (subtraction) between the power of the strong axis and the power of the weak axis; and (iii) angle=angle of the strong axis.

Several methods could be applied in order to verify that the measured MDBA is not too short or too long. In this method, referred to herewith as "blur back", the subject pushes back the screen from the MDBA to a distance equivalent to a one diopter blur. For example, a measured MDBA of 33 cm, indicating a power of 3 Diopters, would be instructed to push back to 50 cm, corresponding to 2D. The anticipated blur of 1 diopter should result with a reduction of 0.2-0.3 [logmar] to the visual acuity.

Another method for the verification of the MDBA is a chromatic method in which the color of the target is switched to a short wavelength corresponding color while maintaining the same MDBA distance. The chromatic aberration of the eye would result in a myopic shift, hence preventing an over minus result. A sharp short wavelength related color image would indicate a too short MDBA result. Using a long wavelength related color would verify, according to the same principle, that the MDBA is not too long, preventing an over plus. All methods of verification could be applied to all the parameters being measured at any stage of the examination.

Figures 13A, 13B:
FIGS. 13A and 13B show how black and white (BW) target images of optotype letters can be used for visual acuity measuring, according to some embodiments of the invention.

FIG. 13A shows a BW target image 30 of letters for visual acuity (VA) measuring through measuring of coarse estimated sphere equivalent power (SEP) of subjects' eyes, according to some embodiments of the invention. The basic target image 30 is composed of a number of letters (Snellen optotype letter proportions for instance) with a certain gap between each letter.

The SEP test is performed when the target image 30 is located at fixed position such as 1 m (or more) from the subject. Myopic subjects will see the target with a certain degree of defocus. The target image 30 size will be changed until its size is not correlated with a minimum resolution acuity (MAR) angle. Each letter is composed of 5 MAR elements usually, and is partly recognized when the defocus blur is coarsely equal to letter size. The subject should see a blurred target at distance exceeding his/her MDBA (e.g. 2 m→best focus only for myopia of −0.5 D where larger myopes will see it blurry), therefore not stimulating accommodation.

The starting size of the letters in the target image 30 (or any other opometric form—Landolt C, Illiterate E etc) of the target is 6/6 (each letter subtending angle of 5 arcmin). The target is enlarged until the subject recognizes about 50% of letters. In some embodiments, the coarse MDBA is related to size of letter chosen according to the table in FIG. 13B.

Alternately, the subject may be presented with a number of lines of optotypes of increasing size seen simultaneously on the screen, rather than presenting a single line that is enlarged until the subject is able to recognize 50% of the letters as described above in respect to the target image 30 of FIG. 13A. The subject is then asked to read the smallest readable line.

This image 30 can also be used for a coarse estimation of the SEP of the subject for screening out subjects having a SEP of a diopter that exceeds a predefined value. If the SEP is too high (e.g. greater than 9 Diopters (D)) of myopia then the computerized examination may not be able to provide an accurate enough SEP measuring and the subject may be denied of this service of the system. If the SEP is within a permitted range of diopters the application may allow the subject to continue with the examination.

FIGS. 14A and 14B show a target image 31a of two sets of the same letters one over a blue background and the other over a red background for measuring SEP of subjects eyes, according to some embodiments of the invention. FIG. 14A shows the target image 31a as displayed over the screen for testing SEP; and FIG. 14B shows an image 31b of how the target image 31a will be perceived at MDBA distance when only the letters in blue are blurred and the red ones are readable. This test and target image 31a are designed to allow the subject to easily recognize the MDBA position at a greater accuracy.

The target image 31a is composed of two adjacent rectangular patches of red and blue (or green) colors. On each patch there is a number of letters (Snellen optotype letter proportions for instance) with a certain gap between each letter. This test can only be performed for subjects that do not have color-blindness. The starting size of letters (or any other optometric form—Landolt C, Illeterate E etc) of the target image 31a is 6/6 (each letter subtending angle of 5 arcmin). The test for SEP measuring relies on chromatic dispersion of eye optics, with red target seen in focus further than the blue (green) one. For this reason the subject may still be able to read the letters over the red background when the letters over the blue background become completely blurred and unreadable. The blue background can be replaced by a green background.

In this phase of SEP detection, the subject is instructed to hold the display (with target image 31a) such that letters on both red and blue or green patches are blurred and unreadable. Then the subject is instructed to move the display closer (while target size is adjusted to keep same angle continuously or in steps) until he/she can read all the letters on the red patch (black letters with red background), while on the blue patch (or green) the subject cannot read all the letters (the stopping condition). This way the subject is not tempted to apply accommodation, and stops the first time red letters are readable at the MDBA. The resulted distance is then measured from the image taken by the camera of the system and image analysis thereof, as explained above, where the MDBA distance is then converted to spherical equivalent power with Power=1/mdba If the subject cannot find distance he/she sees the 6/6 letters, the subject may ask to enlarge the letters to 6/9 size through the application UI (each letter subtending angle of 7.5 arcmin), and the procedure is repeated.

FIGS. 15A and 15B show a striped papillon target image 32a having green arch-shaped stripes over black background with one of the arch-shaped stripes in each side colored in red, according to some embodiments of the invention: FIG. 15A shows the papillon target image 32a as displayed over the screen for measuring the MDBA; and FIG. 15B shows the papillon target image 32b as it would appear passing the MDBA where the red arch shaped stripes appear to turn yellowish.

The target image 32a is constructed of two sectors of a concentric ring. The angle of each sector can be 5°-45°. Most arched stripes are green while one or several are colored red. The choice of two colors made in this example is such that mixing colors by blur creates a distinguishable color (red in this case). In addition, due to chromatic aberration of eye, when the distance between the subject and the target image reaches the distance of minimal blending (coming from distance to near), the red stripe reaches its sharpest point first. The green stripes are defocused yet and blend the red therein—changing the red into yellow. At closer distance the red is defocused and contributes to color change of the green arches. The stopping point is defined as the point where the yellow disappears and red color appears (32c)—at this location the green is still defocused, therefore the subject should not start accommodation yet. This distance is therefore the MDBA distance for the near cyl. The orientation of the target image 32a may be adapted to be perpendicular to astigmatic angle found in previous astigmatism tests.

In some tests made, the in-focus point spread function half-width is about two minarc. That is also the just noticeable blur size—0.15-0.2[diopters]. Since the noticeable chromatic dispersion is about 0.25 D [diopter], taking the arched stripes of red and green as about same number, 2-4 minarc, promises sufficient color blending effect.

According to some embodiments, when using papillon target images such as image 32a the subject may be instructed through the application software and hardware tools to bring the display or himself away until the red ring (in our example) becomes yellowish, and then to start bringing it closer until he starts to see red again The distance at this point is then automatically measured and taken as the MDBA distance (the estimated one over the stronger astigmatic power ("near cyl")).

Figure 16A:
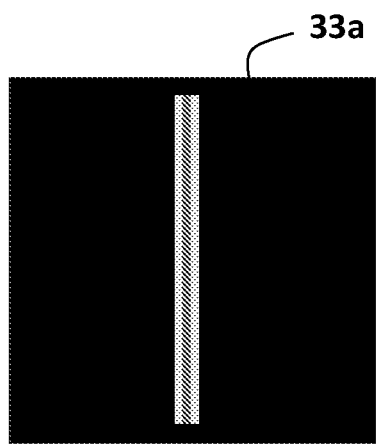
FIGS. 16A and 16B show a straight three-stripes target image having green side stripes over and a middle red stripe black background, according to some embodiments of the invention.
Figure 16B:
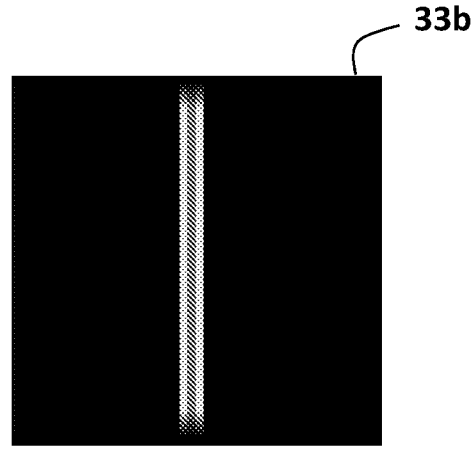

FIGS. 16A and 16B show a straight three-stripes target image having green side stripes over and a middle red stripe black background, according to some embodiments of the invention: FIG. 16A shows the target image 33a as displayed over the screen for measuring astigmatism; and FIG. 16B shows the target image 33b as it would appear for a subject having a 180 degrees astigmatism.

Figure 17A:
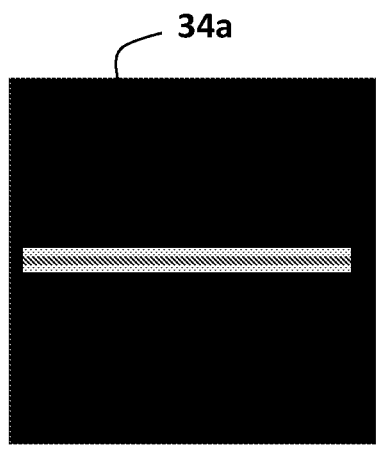
FIGS. 17A and 17B show another straight three-stripes target image having green side stripes over and a middle red stripe black background, according to some embodiments of the invention.
Figure 17B:
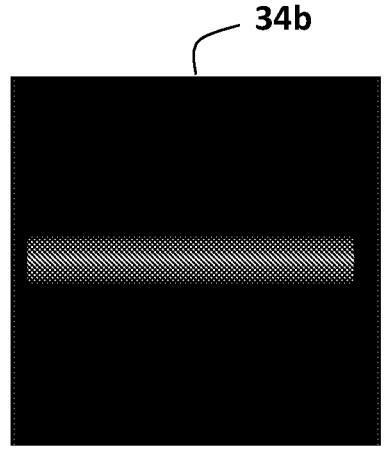

FIGS. 17A and 17B show another straight three-stripes target image 34a having green side stripes over and a middle red stripe black background, according to some embodiments of the invention: FIG. 17A shows the target image 34a as displayed over the screen for measuring astigmatism; and FIG. 17B shows the target image 34b as it would appear for a subject having a 180 degrees astigmatism.

Figure 18A:
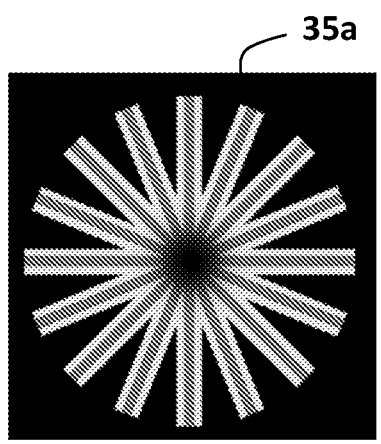
FIGS. 18A and 18B show a colored "sun" target image having multiple stripe target images combined, where each stripe of the sun target image has green side stripes over and a middle red stripe black background, according to some embodiments of the invention.
Figure 18B:
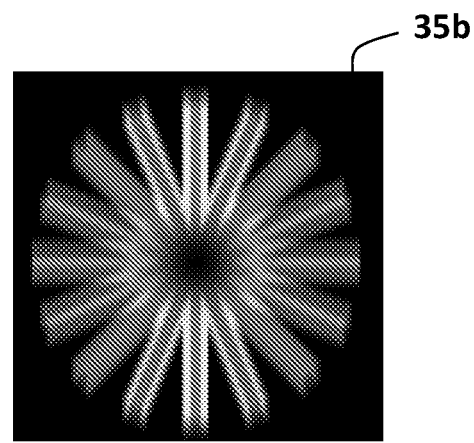

FIGS. 18A and 18B show a colored "sun" target image 35a having multiple stripe target images combined, where each stripe of the sun target image has green side stripes over and a middle red stripe black background, according to some embodiments of the invention: FIG. 18A shows the sun target image 35a as displayed over the screen for measuring astigmatism; and FIG. 18B shows the sun target image 35b as it would appear for a subject having a 180 degrees astigmatism. The striped target image 33a of FIG. 16A is used to construct the sun like shape of the target image 35a shown in FIG. 18A. The basic target building block as shown in FIG. 16A is composed of pair of green side stripes and single red stripe in the middle over a black background forming black gaps between the side green stripes and the red one. When viewed with astigmatic refractive error a certain color blending can occur such as illustrated in FIG. 17B for a 180 degrees astigmatism. The blending depends on properties of the building block. In FIGS. 16A and 17A the shapes are made of three stripes of green-red-green. In other similar sun target images the green-red-green stripes have some more gap between them. In FIG. 17B the 0° shapes are undergone an astigmatic blur of 90, wherein a greenish strip was created in the middle.

When shapes coincide with axis of astigmatic blur, no blending appears (FIG. 16B). The subject can distinguish very easily what is the axis of astigmatism given simultaneously multiple of building blocks in various orientations such as in the sun target image 35a. Due to chromatic aberration of eye, when the target approaches the distance of minimal blending (coming from distance to near), the red stripe reaches its sharpest point first. Each green stripe is defocused yet and blends the red at its location, which changes it into yellow. At closer distance the red is defocused and contributes to color change of green. The stopping point is defined when the yellow disappears and red color appears—at this location the green is still defocused, therefore the subject should not start accommodate yet. This distance is therefore the considered to be the MDBA.

The in-focus point spread function half-width is about 2 minarc. That is also the just noticeable blur size—0.15-0.2 D[diopters]. Since the noticeable chromatic dispersion is about 0.25 D [diopter], taking the stripes of red and green as about same number, 2-4 minarc, promises sufficient color blending effect. This situation is demonstrated in FIGS. 18A and 18B, where angular separation between each blocks is 90°/4=22.5°. It is possible to change the number of blocks (striped images), for instance to four, with resulting angular separation between each block of 90°/3=30° (resembling the clock).

This test can obviously only be performed in case the subject does not suffer from color-blindness.

According to some embodiments, in the phase of detection of astigmatic angle, the subject is instructed to hold the display at distance in which all the sun target image 35a is blurry. The subject is asked to bring the display closer until the color of at least one of targets stripes turns to red from yellow in a distinct manner. If the subject cannot see at least one of them, the size of target is changed and the subject is asked to try again. This can be done several times. The resulted angle is the angle of weaker astigmatic power ("far cyl"). The cylinder axis is perpendicular to the resulted angle. The reported distance is the estimated one over the weaker astigmatic power.

Figure 19A:
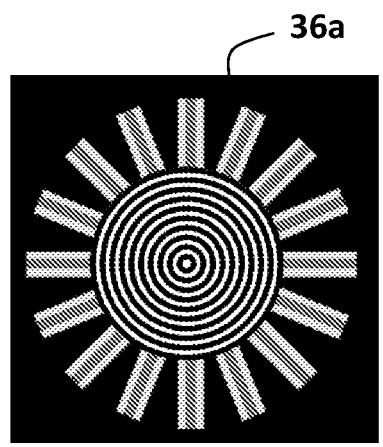
FIGS. 19A and 19B show a combined sun target image including the sun and a BW concentric ring image at the middle thereof, according to some embodiments of the invention.
Figure 19B:
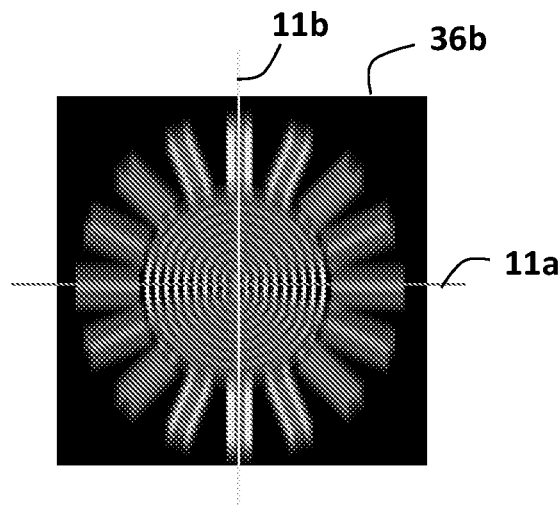

FIGS. 19A and 19B show a combined sun target image including the sun and a BW concentric ring image at the middle thereof, according to some embodiments of the invention: FIG. 19A shows the combined sun target image 36a as displayed over the screen for measuring astigmatism; and FIG. 19B shows the combined sun target image 36b as it would appear for a subject having a 180 degrees astigmatism.

The purpose of this combined target image 36a is to refine identification of the astigmatism axis. Using the chromatic sun shape provides a coarser resolution and therefore the combined target image 36a can refine that resolution by using the BW concentric ring shape simultaneously within the same target image.

According to some embodiments, the subject in this case is presented with the target image 36a after coarse axis estimation. The bright region in the concentric rings shape of the combined target image 36a and the non-blurred papillon-shaped part of the sun image are perpendicular. The subject is instructed to rotate the overlaid reticule markers 11a and 11b to match these targets indicators i.e. to the central axis of the clear papillon shape of the concentric ring target that has formed and the clearest stripe of the sun image as shown in FIG. 19B.

Figure 20A:
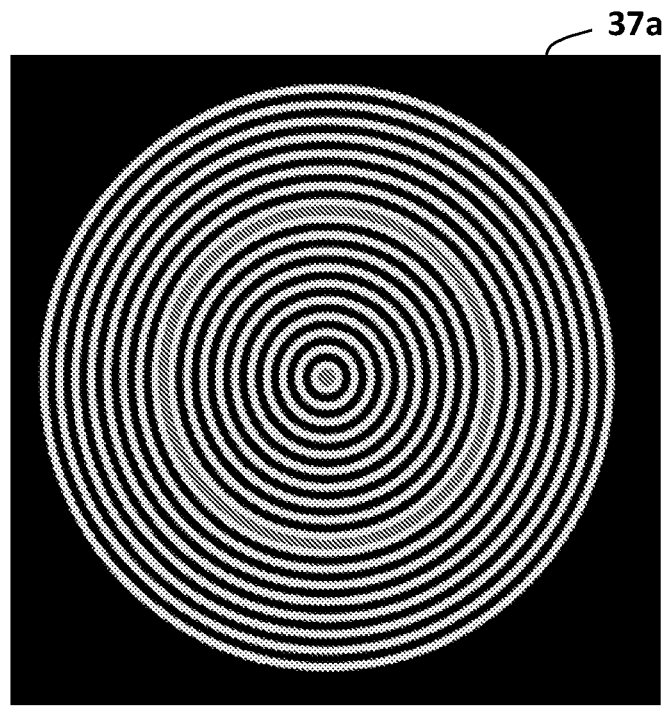
FIGS. 20A and 20B show a colored "concentric rings" target image having multiple green rings with one of the rings colored red over a black background, according to some embodiments of the invention.
Figure 20B:
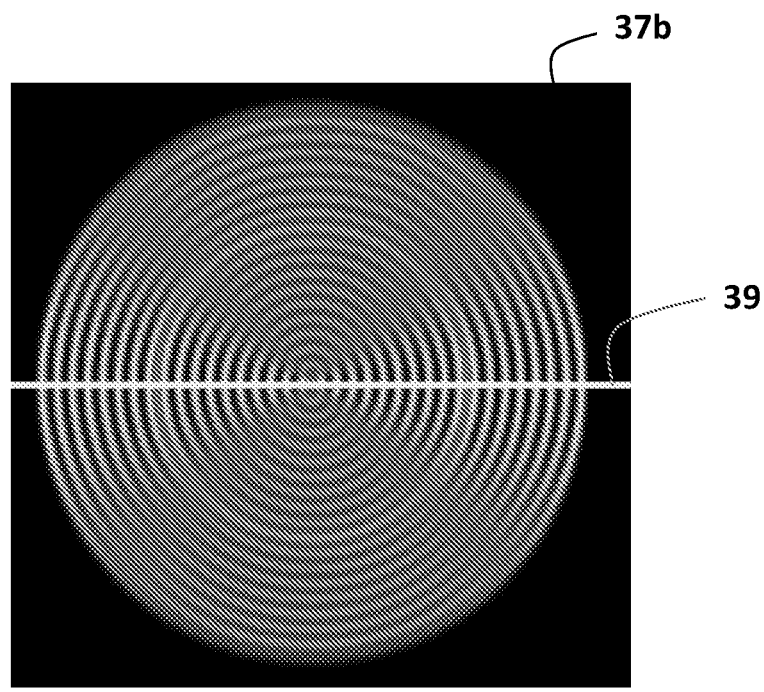

FIGS. 20A and 20B show a colored "concentric rings" target image 37a having multiple green rings with one of the rings colored red over a black background, according to some embodiments of the invention: FIG. 20A shows the concentric rings target image 37a as displayed over the screen for measuring astigmatism; and FIG. 20B shows the concentric rings target image 37b as it would appear for a subject having a 90 degrees astigmatism with a bat marker placed by the subject over the image in a location indicating the center of the papillon shape appearing clearer as input feedback according to which the astigmatism angle of the subject can be deduced.

The target image may include only partial area of the concentric rings achieving the same effect.

The target image 37a has concentric rings colored in green over a black background with addition single/several red rings. This target image 37a is used to further refine the astigmatism axis identification. This target image 37a reaches MDBA according to the same principle explained in "Papillon" target.

The subject is presented with the target image 37a after coarse axis estimation. The subject is instructed to hold the display at a distance in which all the target image 37b is blurry. The subject is then instructed to bring the display closer until reaching a certain stopping point according to a predefined condition. Due to chromatic aberration of eye, when the target approaches the distance of minimal blending (coming from distance to near), the red stripe reaches its sharpest point first. The green stripe is defocused yet and blends the red at its location—changes it into yellow. At closer distance the red is defocused and contributes to color change of green. The stopping point is therefore defined at a distance in which the yellow disappears and red color appears. At this location the green is still defocused, therefore the subject should not start accommodation yet. This distance is therefore the MDBA. The subject may be instructed to rotate the marker with an indicator line 39 to correct orientation. The in-focus point spread function half-width is about 2 minarc. That is also the just noticeable blur size—0.15-0.2[diopters]. Since the noticeable chromatic dispersion is about 0.25 [diopter], taking the stripes of red and green as about same number, 2-4 minarc, promises sufficient color blending effect.

Figure 21A:
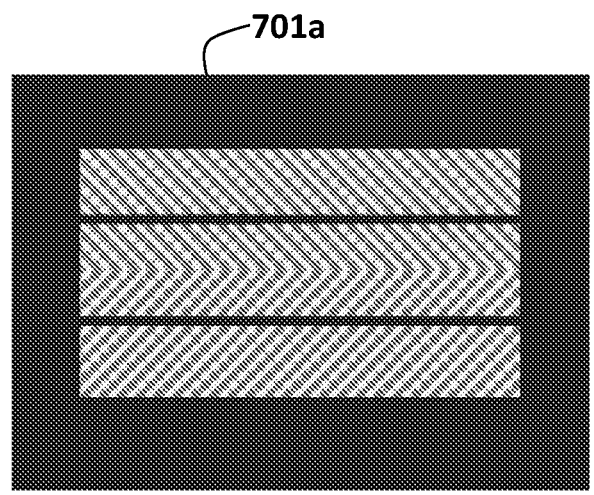
FIGS. 21A and 21B show two different target images, each having a unique pattern for a validation test also referred to herein as "the African test", according to some embodiments of the invention.
Figure 21B:
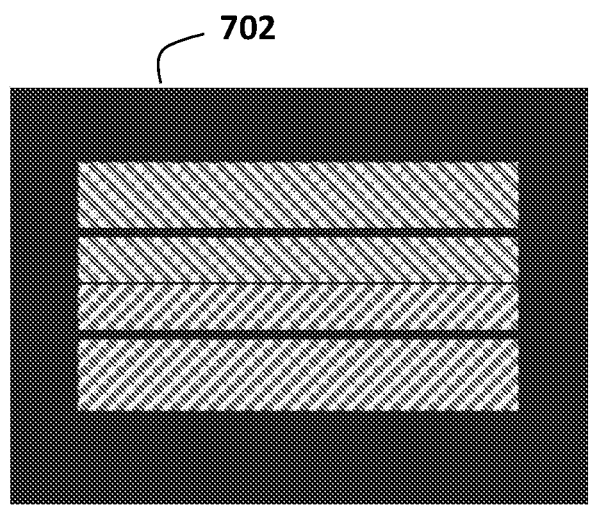

FIGS. 21A and 21B show two different target images 701a and 702, each having a unique pattern used for an optional validation test also referred to herein as "the African test", according to some embodiments of the invention. FIG. 21A shows a target image 701a having interchanging sets of rows of yellow and red elliptic units (also referred to herein as "building blocks") arranged in rows. The target image is sliced by two upper and lower dark green stripes with no middle dark stripe (image 701a), or with a middle dark green stripe of a thinner thickness than the upper and lower stripes (image 702). The shapes are chosen to produce spatial pattern with minimal contrast in presence of symmetrical/spherical blur: the basic periodical building block (image 710) consists of an equally spaced contrast color in all directions and when symmetrical blur occurs the two main colors are averaged producing uniform pattern. Perturbing the periodic structure (as in the middle of image 701a) shifts same colors closer in a certain dimension. In this dimension the shapes will not change color significantly under directional blur such as cylindrical blur coherent with that dimension. Another method to generate a unique pattern under directional blur depicts at image 701/702 where the target image is sliced by two upper and lower thick dark green stripes. In presence of directional blur (that is coherent with the aforementioned dimension) the two colors are blurred into the dark stripe with no mutual blend. This would create a yellow—red alternating stripe pattern given black background. Since the gray levels of such pattern are low, a minor change in background color could change color of pattern. Using dark green color will effect in green-red alternating pattern (image 701*b*).

Figure 22:
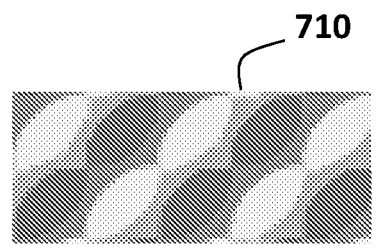

FIG. 22 shows a zoomed image of the pattern 710 of the target images 701*a* and 702 of FIGS. 21A and 21B tilted in one of the possible interchanging directions.

Figure 23:
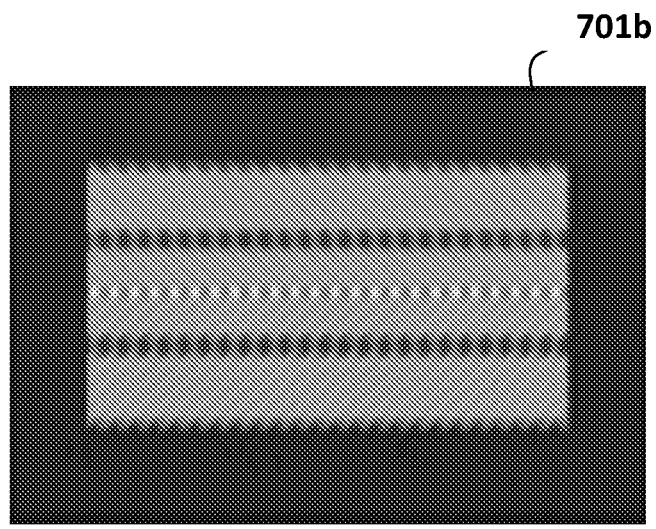
FIG. 23 shows how the target image of FIG. 21A would appear at the distance that the subject is instructed to stop. This happens at specific distance where sphere and cyl combination produces a known blur.

FIG. 23 shows how the target image of FIG. 21A would appear at the distance that the subject is instructed to stop (MDBA) where the presence of the alternating lower and upper green-red patterns and middle red-yellow pattern are best apparent. This happens at specific distance where sphere and cyl combination produces a known blur.

Figure 24A:
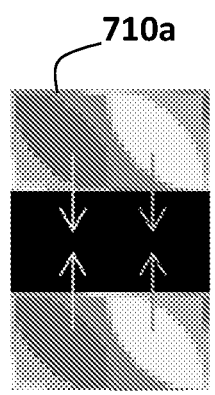
FIGS. 24A and 24B show a zoomed image of the pattern of the target image of FIG. 21A.
Figure 24B:
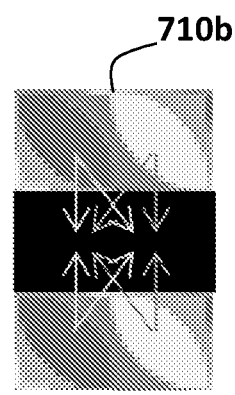

FIGS. 24A and 24B show a zoomed image of the pattern of the target image 701*a* of FIG. 21A.

The images 701*a* or 702 are used to validate the already measured spherical and cylindrical error of the subject. The target image 701*a* for instance is displayed over the screen and the subject is requested to locate himself/herself in front of the screen at the MDBA distance where the alternating red-green and red-yellow patterns are best apparent (image 701*b*). At this stopping point a blur is composed from both spherical and cylindrical contributions. From evaluating two, or more, similar targets that differ in size it is possible to relate the obtained distances combinations to a specific spherical and cylindrical error. These image sizes are determined according to the previous spherical and cylindrical error (astigmatism) testing. In case the subject has astigmatism of 90 degrees, the image would appear an image 701*b* as shown in FIG. 23 at the stopping point position of the particular subject. In this image appearance 701*b* the upper and lower thicker dark green stripes of the original target image 701*a* would appear to have brown/red and green alternating blocks and the middle dark stripe will instead have alternating yellow and red blocks.

The target image 701*a* is affected differently by spherical error blur and astigmatic blur. Therefore, for any other astigmatic blur (other than 90 degrees) the orientation and size of the target image 701*a* will be orientated, in order to obtain these profound effects.

The areas of pattern in the target image 701*a* that are background become uniform for blur size of close to 2×h. It is expected since elliptical shapes from neighbor rows are averaged as illustrated in FIGS. 24A and 24B. The two dark green lines, being 1×h high, get coloring from neighbor rows: red and greenish-yellowish patches are created by blur. Their contrast is much lower than for astigmatic blur, since in astigmatic case the red is created only from red, and greenish for the yellow lower and upper rows (FIG. 24B), while for spherical only refractive error building blocks of the pattern red and yellow start to blend into each other and reduce contrast as sphere blur continues to grow (FIG. 24A). Presence of Spherical and Astigmatic blur simultaneously: This is the case when the blur spot is an ellipse instead of circle disk. Therefore, vertical component is enforcing the appearance of all above-mentioned (three) effects, while the horizontal component weakens. If the size of target image 701*a* is constant, and is moved axially, for each location: (a) different blurring effect is resulted; (b) the mutual strength of vertical and horizontal components is changed; and (c) the ratio of blur spot to "h" is changed.

Relation of blur to refractive error: Since the blur is significant, the geometrical optics relation is valid:

$$\emptyset[\text{rad}] = D_{pupil}[m] \times \Delta L$$

Where $\emptyset$ is the angular size of blur disc; $D_{pupil}$ is the pupil diameter and $\Delta L$ is the .dioptric error.

$$[\text{diopter}]\emptyset[\text{minarc}] = 60\frac{180}{\pi}D_{pupil}[m] \times \Delta L[\text{diopter}]$$

The target image 701*a* or 702 is rotated to the same angle as that found in the .concentric circles but at 90 degrees to the sharp line on the glowing sun.

In some embodiments the test procedure includes the following steps: (i) the subject is asked to bring the display away until the whole target is blurry, and then (ii) to start bringing the display closer until he sees the aforementioned effect, (iii) Then the size of a target is changed and the subject is asked to repeat the test. The procedure is performed several times with targets scaled differently. The stopping point with each such iteration is different because of changes in viewing angle that "h" (image 710) subtends and in the weights of spherical and cylindrical components of blur spot. Several distances are recorded correspondingly. Since the size and characteristics of the target image are known, they are used to calculate the astigmatic power and to refine previous results of spherical and astigmatic power.

Figure 25:
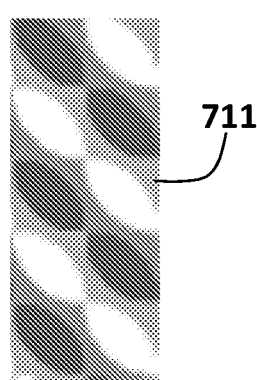
FIG. 25 shows another optional building block for a pattern for validation test, according to other embodiments of the invention.

FIG. 25 shows another optional building block 711 for a pattern for validation test, according to other embodiments of the invention.

Figure 26:
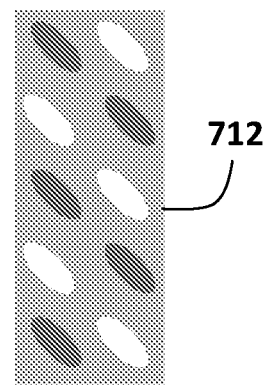
FIG. 26 shows yet another optional building block for a pattern for validation test, according to other embodiments of the invention.

FIG. 26 shows yet another optional building block 712 for a pattern for validation test, according to other embodiments of the invention.

Figure 27A:
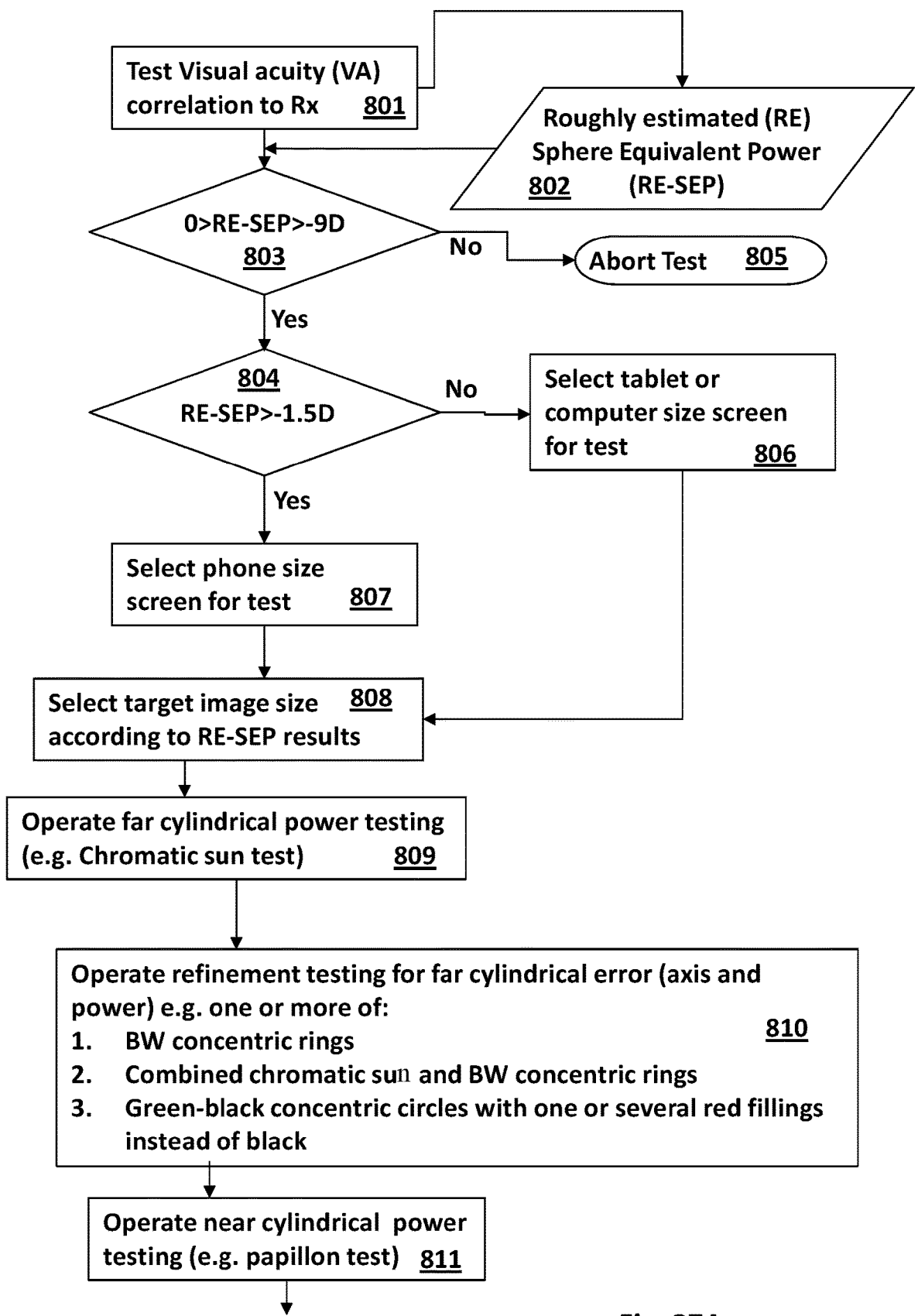
FIGS. 27A and 27B show a flowchart illustrating a complete process of an optometric test for measuring SEP and far cyl and near cyl of a subject, using the target images provided above, according to some embodiments of the present invention.
Figure 27B:
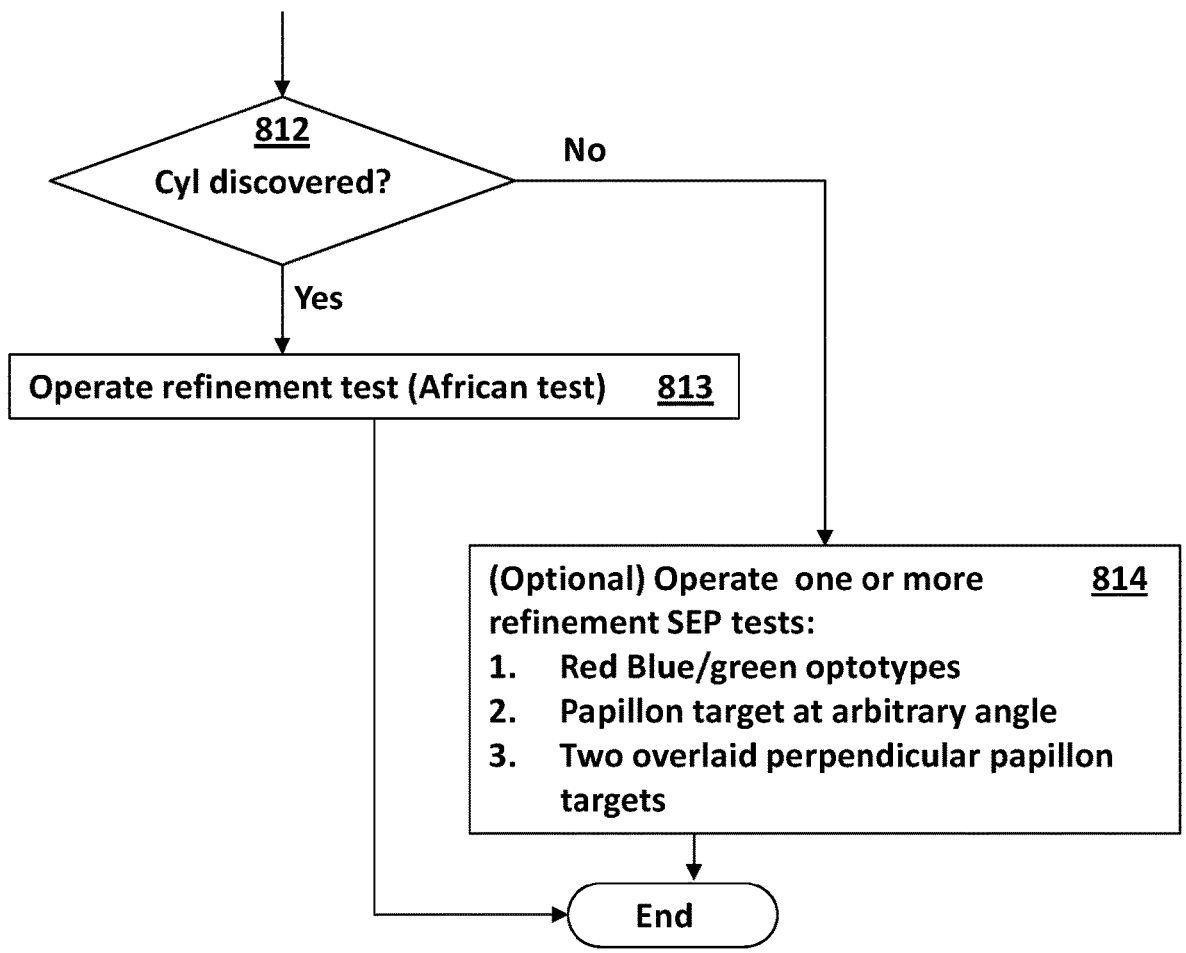

FIGS. 27A and 27B show a flowchart illustrating a process of an optometric test for measuring refractive error of a subject's eye including measurements of SEP and astigmatism, using some or all of the various target images of the present invention specified above, according to some embodiments of the present invention: FIG. 27B is a continuation of the process of FIG. 27A. The process is carried out by the system using the designated software application operable over the personal device of the subject such as the subject's tablet or smartphone using a camera sensor of the personal device or an external sensor controllable by the personal device.

Initially a visual acuity (VA) test is performed 801, e.g. using the letters target image(s) such as images 30 and/or 31*a*. The resulting roughly estimated SEP (RE-SEP) data 802 from the VA test may be saved optionally along with the MDBA of the subject. The VA test may be preceded with a calibration test for allowing measuring, for example, a facial element of the subject such as the width of the tested or non-tested eye for the distance metering as explained above. Alternatively the subject may be required to hold the reference element over the non-tested eye for the distance metering.

If the RE-SEP value is within a predefined dioptric range (e.g. between 0 and −9 Diopters) 803 then the subject is allowed to use the application for refractive error testing. If the RE-SEP exceeds the range then the application may not be able to carry an accurate enough measuring and therefore the process may be terminated 805.

The application further checks if the RE-SEP exceeds a predefined threshold value 804 for selecting the appropriate screen size (and therefore appropriate personal device) required for testing the subject 806-807.

Once the screen size and therefore the personal device type is selected, the appropriate target image size for the cylindrical error testing is selected 808 according to the RE-SEP results and the far cylindrical error testing is operated 809 e.g. by using the chromatic test as explained in respect to FIGS. 15A-20B. The coarser far cylindrical error testing may involve using the chromatic sun target image (FIGS. 18A-18B) and one or more refinement tests 810 using for example one or more of: (1) the BW concentric rings target image (FIGS. 4J-4L); (2) the combined chromatic sun and BW concentric rings target image (FIGS. 19A-19B); and/or (3) the chromatic concentric rings target image (FIGS. 20A-20B).

A near cylindrical error testing is also operated 811 using for example, the papillon target image (FIGS. 15A-15B). If cylindrical error is detected 812 a refined test for cylindric power and angle is operated 813, e.g. using the African test as explained in relation to FIGS. 21A-23.

If no cylindrical error is detected 812 a refined SEP testing may be operated e.g. by using one or more tests using at least one of the following target images: (1) the red and blue/green letters tests 814 (FIGS. 14A-14B) (2) the papillon target image (FIGS. 15A-15B) at arbitrary angles; and/or (3) a target image showing two overlaid perpendicular papillon.

In any of the above described tests the UI of the application allows instructing the subject along the test while providing input platform for inputting data and operational commands such as for operating the camera for capturing the image of the subject's face when the subject feels he/she has reached the MDBA position and the like. The application may also be configured such that it can instruct the subject to correct the way he/she holds the personal device or camera. The instructions can be visually displayed; and/or audio outputted such as through pre-recorded voice commands; and/or indicated through tactile output e.g. by using vibration options of the personal device. For example to indicate to the subject to tilt the device to a specific direction it may increase vibrations when tilting in the right direction and weaken the vibrations when tilting in an opposite direction.

Any one or more target images may be used of any shape, symmetry and coloration for measuring any one or more aspects of the subject's refractive error. The present invention is not limited to the target images illustrated above and other new or known target images can be used. The target images presented in this application can also be modified, colored differently or have different lines widths or textures.

According to some embodiments of the present invention is provided a correction process for correcting cylindrical and spherical power. The correction process comprising the steps of: receiving astigmatism angle, cylindrical power and spherical power resulting from previous testing of the subject; displaying the unique pattern target image over the display area rotated to an angle of astigmatism of the subject, according to the received astigmatism angle, said unique pattern target image is displayed over the display area at at least two sizes, each size calculated according to the received cylindrical power and spherical power. For each size of the displayed unique pattern target image, instructing the subject to distance from the target image until recognizing a predefined visual effect, for each size of the displayed unique pattern target image, measuring the distance between the unique pattern target image and the tested eye of the subject and recalculating cylindrical power and spherical power according to the measured distances.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments and/or by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

Although the invention has been described in detail, nevertheless changes and modifications, which do not depart from the teachings of the present invention, will be evident to those skilled in the art. Such changes and modifications are deemed to come within the purview of the present invention and the appended claims.

REFERENCES

1. R. BEDFORD and G. WYSZECKI, "Axial Chromatic Aberration of the Human Eye," J. Opt. Soc. Am. 47, 564_1-565 (1957).

What is claimed is:

1. A non-transitory storage medium comprising computer-executable instructions operable to, when executed by at least one processor, cause a computing device to:
   trigger displaying of at least one target image over a display area;
   trigger an instruction to a subject to change a distance between an eye of the subject and said display area to identify a subjective distance, at which said subject is to clearly recognize a predefined visual element of said target image using said eye;
   determine a calculated parameter associated with a refractive error of the eye of the subject based on input data indicative of the subjective distance, and based on an attribute of the predefined visual element of said target image; and
   provide an output based on the calculated parameter.

2. The non-transitory storage medium of claim 1, wherein the instructions, when executed, cause the computing device to identify that the eye of the subject is at the subjective distance from the display area based on feedback from the subject indicating that the subject is to clearly recognize the predefined visual element of said target image using said eye.

3. The non-transitory storage medium of claim 1, wherein the instructions, when executed, cause the computing device to process subjective feedback from the subject to identify the subjective distance out of a plurality of distances between the eye of the subject and the display area.

4. The non-transitory storage medium of claim 3, wherein the instructions, when executed, cause the computing device to trigger an instruction to the subject to change the distance between the eye of the subject and said display area according to the plurality of distances.

5. The non-transitory storage medium of claim 3, wherein the instructions, when executed, cause the computing device to dynamically change the attribute of the predefined visual element of the target image according to the plurality of distances.

6. The non-transitory storage medium of claim 1, wherein the instructions, when executed, cause the computing device to:
   trigger a first instruction to the subject to change the distance between the eye of the subject and said display area to identify a first subjective distance, at which said subject is to clearly recognize a first predefined visual element of a first target image using said eye;
   trigger a second instruction to the subject to change the distance between the eye of the subject and said display area to identify a second subjective distance, at which said subject is to clearly recognize a second predefined visual element of a second target image using said eye; and
   determine the calculated parameter associated with the refractive error of the eye of the subject based on input data indicative of the second subjective distance.

7. The non-transitory storage medium of claim 6, wherein the instructions, when executed, cause the computing device to determine a first parameter of the eye of the subject based on input data indicative of the first subjective distance, and to determine a second parameter of the eye of the subject based on the input data indicative of the second subjective distance.

8. The non-transitory storage medium of claim 7, wherein the first parameter comprises a dioptric power parameter, and the second parameter comprises an astigmatism parameter.

9. The non-transitory storage medium of claim 7, wherein the instructions, when executed, cause the computing device to set an attribute of the second target image based on the first subjective distance.

10. The non-transitory storage medium of claim 9, wherein the attribute of the second target image comprises an angle of the second predefined visual element.

11. The non-transitory storage medium of claim 1, wherein said subjective distance comprises a subjective maximum distance of best acuity (MDBA), said subjective MDBA comprising a maximum distance between the eye of the subject and said target image, at which the subject is to clearly recognize the predefined visual element of said target image using said eye.

12. The non-transitory storage medium of claim 1, wherein the attribute of the predefined visual element comprises an angle of the predefined visual element.

13. The non-transitory storage medium of claim 1, wherein the attribute of the predefined visual element comprises a color of the predefined visual element.

14. The non-transitory storage medium of claim 1, wherein the attribute of the predefined visual element comprises a spatial frequency of features of the predefined visual element.

15. The non-transitory storage medium of claim 1, wherein the attribute of the predefined visual element comprises a rotational axis of the predefined visual element.

16. The non-transitory storage medium of claim 1, wherein the target image comprises a chromatic target image.

17. The non-transitory storage medium of claim 1, wherein the target image comprises a circularly symmetric or rotationally symmetric target image.

18. The non-transitory storage medium of claim 1, wherein said input data comprises 3-dimensional (3D) sensor information from a 3D sensor.

19. The non-transitory storage medium of claim 1, wherein said input data comprises sensor information from a sensor, the sensor information comprising at least one of distance information or acceleration information indicative of the subjective distance.

20. The non-transitory storage medium of claim 1, wherein said input data comprises image information of an image captured by an image sensor.

21. An apparatus comprising:
   a display configured to display at least one target image over a display area;
   a user interface to provide an instruction to a subject to change a distance between an eye of the subject and said display area to identify a subjective distance, at which said subject is to clearly recognize a predefined visual element of said target image using said eye;
   a sensor to provide data indicative of the subjective distance; and
   a processor configured to determine a calculated parameter associated with a refractive error of the eye of the subject based on the data indicative of the subjective distance, and based on an attribute of the predefined visual element of said target image, the processor configured to provide an output based on the calculated parameter.

22. The apparatus of claim 21, wherein the processor is configured to identify that the eye of the subject is at the subjective distance from the display area based on feedback from the subject indicating that the subject is to clearly recognize the predefined visual element of said target image using said eye.

23. The apparatus of claim 21, wherein the processor is configured to process subjective feedback from the subject to identify the subjective distance out of a plurality of distances between the eye of the subject and the display area.

24. The apparatus of claim 21, wherein the processor is configured to:
  trigger a first instruction to the subject to change the distance between the eye of the subject and said display area to identify a first subjective distance, at which said subject is to clearly recognize a first predefined visual element of a first target image using said eye;
  trigger a second instruction to the subject to change the distance between the eye of the subject and said display area to identify a second subjective distance, at which said subject is to clearly recognize a second predefined visual element of a second target image using said eye; and
  determine the calculated parameter associated with the refractive error of the eye of the subject based on data indicative of the second subjective distance.

25. The apparatus of claim 21, wherein the sensor comprises a 3-dimensional (3D) sensor to provide 3D data indicative of the subjective distance.

26. A method comprising:
  triggering displaying of at least one target image over a display area;
  triggering an instruction to a subject to change a distance between an eye of the subject and said display area to identify a subjective distance, at which said subject is to clearly recognize a predefined visual element of said target image using said eye;
  determining a calculated parameter associated with a refractive error of the eye of the subject based on input data indicative of the subjective distance, and based on an attribute of the predefined visual element of said target image; and
  providing an output based on the calculated parameter.

27. The method of claim 26 comprising processing subjective feedback from the subject to identify the subjective distance out of a plurality of distances between the eye of the subject and the display area.

28. An apparatus comprising:
  means for triggering displaying of at least one target image over a display area;
  means for triggering an instruction to a subject to change a distance between an eye of the subject and said display area to identify a subjective distance, at which said subject is to clearly recognize a predefined visual element of said target image using said eye;
  means determining a calculated parameter associated with a refractive error of the eye of the subject based on input data indicative of the subjective distance, and based on an attribute of the predefined visual element of said target image; and
  means for providing an output based on the calculated parameter.

29. The apparatus of claim 28 comprising means for identifying that the eye of the subject is at the subjective distance from the display area based on feedback from the subject indicating that the subject is to clearly recognize the predefined visual element of said target image using said eye.

* * * * *